United States Patent
Shusta et al.

(10) Patent No.: US 10,590,393 B2
(45) Date of Patent: Mar. 17, 2020

(54) RETINOIC ACID ENHANCED HUMAN STEM CELL DERIVED BLOOD BRAIN BARRIER MODEL

(71) Applicant: Wisconsin Alumni Research Foundation, Madison, WI (US)

(72) Inventors: Eric V. Shusta, Madison, WI (US); Sean P. Palecek, Verona, WI (US); Ethan S. Lippmann, Madison, WI (US); Samira M. Azarin, Chicago, IL (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 13/793,466

(22) Filed: Mar. 11, 2013

(65) Prior Publication Data

US 2014/0127800 A1    May 8, 2014

Related U.S. Application Data

(60) Provisional application No. 61/724,072, filed on Nov. 8, 2012.

(51) Int. Cl.
*C12N 5/071* (2010.01)
*C12N 5/0797* (2010.01)

(52) U.S. Cl.
CPC ........... *C12N 5/0697* (2013.01); *C12N 5/069* (2013.01); *C12N 5/0623* (2013.01); *C12N 5/0692* (2013.01); *C12N 2500/90* (2013.01); *C12N 2501/115* (2013.01); *C12N 2501/385* (2013.01); *C12N 2502/08* (2013.01); *C12N 2502/088* (2013.01); *C12N 2506/02* (2013.01); *C12N 2506/45* (2013.01)

(58) Field of Classification Search
CPC .... C12N 5/0697; C12N 5/0623; C12N 5/069; C12N 2500/90; C12N 2502/08
See application file for complete search history.

(56) References Cited

U.S. PATENT DOCUMENTS

| | | |
|---|---|---|
| 7,744,879 B2 | 6/2010 | Shusta |
| 7,981,417 B2 | 7/2011 | Shusta |
| 8,034,607 B2 | 10/2011 | Shusta |
| 8,293,495 B2 | 10/2012 | Shusta |
| 2008/0044847 A1* | 2/2008 | Shusta et al. ............ 435/29 |
| 2010/0137158 A1 | 6/2010 | Shusta |
| 2012/0015395 A1 | 1/2012 | Shusta |
| 2012/0277122 A1 | 11/2012 | Shusta |
| 2013/0029419 A1 | 1/2013 | Shusta |

FOREIGN PATENT DOCUMENTS

WO    20111565572 A2    12/2011

OTHER PUBLICATIONS

Stanness et al NeuroReport 1999, 10, 3725-3731.*
Kawaguchi et al (Science, 2007, 315, 820-825.*
Dar et al Circulation. Jan. 3, 2012;125(1):87-99.*
Butt et al Journal of Phsiology, 1990, 429, 47-62.*
Calabria et al Journal of Neurochemistry, 2006, 97, 922-933).*
Lippmann et al Nat Biotechnol. Aug. 2012; 30(8): 783-791.*
Bouillet et al Mech Dev. May 1997;63(2):173-86.*
Lippmann et al Fluids Barriers CNS. 2013; 10: 2, 1-14.*
Reubinoff et al. (2000, Nature Biotechnology, vol. 18, pp. 399-404.*
Ireland KA., Visualizing Human Biology, 3rd Ed., Wiley and Sons Inc., 2008 , 3, p. 527.*
Rhinn et al Development 139, 843-858 (2012).*
Reijo et al. 2009, Differentiation, vol. 78, pp. 18-23.*
Ware et al. 2014, PNAS, vol. 111(12), pp. 4484-4489.*
Daneman et al., The Mouse Blood-Brain Barrier Transcriptome: A New Resource for Understanding the Development and Function of Brain Endothelial Cells, PLoS One, www.plosone.org, vol. 5, Issue 10, Oct. 2010, pp. 1-16.
Ethan S. Lippmann et al.: "Blood-brain barrier modeling with co-cultured neural progenitor cell-derived astrocytes and neurons", Journal of Neurochemistry, vol. 119, No. 3, Nov. 21, 2011 (Nov. 21, 2011), pp. 507-520, ISSN: 0022-3042, DOI: 10.1111/j.1471-4159. 2011.07434.x.
Ethan S Lippmann et al.: "Derivation of blood-brain barrier endothelial cells from human pluripotent stem cells", Nature Biotechnology, vol. 30, No. 8, Jun. 24, 2012 (Jun. 24, 2012), pp. 783-791, ISSN: 1087-0156, DOI: 10.1038/nbt.2247.
Nakagawa S et al.: "A new blood-brain barrier model using primary rat brain endothelial cells, pericytes and astrocytes", Neurochemistry International, Pergamon Press, Oxford, GB, vol. 54, No. 3-4, Mar. 1, 2009 (Mar. 1, 2009), pp. 253-263, ISSN: 0197-0186, DOI: 10.1016/ J.NEUINT.2008.12.002 [retrieved on Dec. 7, 2008].
Ethan S Lippmann et al.: "Modeling the blood-brain barrier using stem cell sources", Fluids and Barriers of the CNS, Biomed Central Ltd, London, UK, vol. 10, No. 1, Jan. 10, 2013 (Jan. 10, 2013), p. 2, ISSN: 2045-8118, DOI: 10.1186/2045-8118-10-2.
Mark R Mizee et al.: "Retinoic Acid Induces Blood-Brain Barrier Development", Journal of Neuroscience, vol. 33, No. 4, Jan. 2013 (Jan. 2013), pp. 1660-1671, XP002720085, ISSN: 0270-6474.

(Continued)

*Primary Examiner* — Anoop K Singh
(74) *Attorney, Agent, or Firm* — Quarles & Brady LLP

(57) ABSTRACT

In one embodiment, the present invention is a method of creating a fully-human blood-brain barrier (BBB) model, comprising the steps of (a) obtaining a mixture of neural cells and brain microvascular endothelial cells (BMECs), wherein the neural cells and BMECs that comprise the mixture were produced from the differentiation of human pluripotent stem cells (hPSCs); (b) purifying BMECs from the mixture of neural cells and BMECs of step (a); and (c) co-culturing the purified BMECs with a cell type selected from the group consisting of pericytes, astrocytes and differentiated neural progenitor cells (NPCs), wherein a blood brain barrier model is created.

6 Claims, 13 Drawing Sheets

(11 of 13 Drawing Sheet(s) Filed in Color)

(56) References Cited

OTHER PUBLICATIONS

International Searching Authority, "Notification of Transmittal of the International Search Report and the Written Opinion of the International Search Authority, or the Declaration" in the application of PCT/US2013/068914, dated Feb. 24, 2014 (Feb. 24, 2014).
World Intellectual Property Organization, "International Search Report" in the application of WO2011/159572, dated Apr. 12, 2012 (Apr. 12, 2012).
L. Altucci, M.D. Leibowitz, et al.; RAR and RXR Modulation in Cancer and Metabolic Disease; (2007) Discovery, vol. 6 Oct. 2007 pp. 793-810—Nature Publishing Group.
H.Gronemeyer, J.Gustafsson, et al.; Principles for Modulation of the Nuclear Receptor Superfamily; (2004) Nature Reviews—Drug Discoveries; vol. 3, Nov. 2004, pp. 950-964.
J.R. Tata; Signalling Through Nuclear Receptors; (2002) Nature Reviews—Molecular Cell Biology; vol. 3, Sep. 2002 pp. 702-710; Nature Publishing Group.

* cited by examiner

[also see A (RA+) in Fig. 4]

[also see E (RA+ & OECM) in Fig. 4]

RETINOIC ACID ENHANCED HUMAN STEM CELL DERIVED BLOOD BRAIN BARRIER MODEL

CROSS-REFERENCE TO RELATED APPLICATIONS

This application claims benefit from U.S. Provisional Application 61/724,072, filed Nov. 8, 2012, which is incorporated herein by reference for all purposes.

STATEMENT REGARDING FEDERALLY SPONSORED RESEARCH

This invention was made with government support under NS052649 and AA020476 awarded by the National Institutes of Health. The government has certain rights in the invention.

BACKGROUND OF THE INVENTION

The blood-brain barrier (BBB) comprises the brain microvascular endothelial cells (BMECs) which line brain capillaries and control trafficking between the bloodstream and neural tissue. These properties are tightly regulated by the surrounding microenvironment (termed the neurovascular unit) throughout BBB development and into adulthood. While this barrier is essential for preserving healthy brain activity, its dysfunction and deregulation is implicated in a number of neurological diseases (Zlokovic, 2008). Moreover, an intact BBB serves as a major bottleneck for brain drug delivery (Pardridge, 2005). Unfortunately, studies involving BBB development and regulation can be difficult and time-consuming to conduct in vivo, and the ability to screen brain-penetrating therapeutics in vivo is restricted to a small number of researchers with technical expertise in such techniques. Thus, researchers often use more accessible platforms, i.e. in vitro BBB models, to study interactions between BMECs and the neurovascular unit and to conduct compound library screens for prospective BBB-permeant drugs.

In vitro BBB models are typically constructed using primary BMECs isolated from animal brain tissue, including bovine, porcine, rat, and mouse (reviewed extensively in (Deli, et al., 2005)). These BMECs are then co-cultured with combinations of cells of the neurovascular unit, such as neurons, pericytes, and/or astrocytes, to upregulate BBB properties (Nakagawa, et al., 2009; Nakagawa, et al., 2007; Weidenfeller, Svendsen, et al., 2007; Lippmann, et al. 2011). Models derived from animal tissue have proved extremely useful in studying various aspects of the BBB, such as developmental and regulatory mechanisms (Daneman, et al. 2009; Daneman, et al., 2010(a); Kuhnert, et al., 2010; Lee, et al., 2003; Wosik, et al., 2007), but it is generally well-accepted that owing to species differences, a robust human BBB model must be developed to screen therapeutics that can prospectively traverse the human BBB in vivo (Cecchelli, et al., 2007). Human BMEC sources for BBB models have previously included biopsied brain tissue (Bernas, et al., 2010); (Rubin, et al., 1991) and immortalized cell lines (Weksler, et al., 2005). Primary human BMECs typically possess moderate barrier properties but their availability and yield are both extremely low and thus this source of material cannot be scaled for large library screens. Immortalized BMECs exhibit prodigious growth from a clonal population but often have poor barrier properties and are thus not optimal for screening therapeutics. From a co-culture perspective, human neurons, astrocytes, and pericytes can also be difficult to obtain from primary tissue sources in large enough quantities for modeling purposes. These collective issues have hindered the creation of a robust and readily accessible human BBB in vitro model for several decades (Deli, et al., 2005).

Applicants' previous work has demonstrated that stem cells may be attractive candidates to replace primary cells in human BBB models. Applicants have shown that human neural progenitor cells (hNPCs) may be differentiated to a defined mixture of neurons and astrocytes capable of inducing BBB properties in rat BMECs (Lippmann, et al., 2011). Further, Applicants recently demonstrated that human pluripotent stem cells (hPSCs), including both human embryonic stem cells (hESCs) and induced pluripotent stem cells (hiPSCs), could be differentiated into endothelial cells possessing BBB properties (Lippmann, et al., 2012).

Needed in the art are fully-human BBB models, modulator-enhanced BBB models, BBB models under optimized media conditions, and BBB models having high absolute values of transendothelial electrical resistance TEER (e.g., >5000 $\Omega \times cm^2$).

SUMMARY OF THE INVENTION

In one embodiment, the present invention relates to a method of creating a fully-human blood-brain barrier (BBB) model, and the method comprises the steps of a) obtaining a mixture of neural cells and brain microvascular endothelial cells (BMECs), wherein the neural cells and BMECs that comprise the mixture were produced from the differentiation of human pluripotent stem cells (hPSCs); b) purifying BMECs from the mixture of neural cells and BMECs of step (a); and c) co-culturing the purified BMECs with a cell type selected from the group consisting of pericytes, astrocytes and differentiated neural progenitor cells (NPCs), wherein a blood brain barrier model is created.

In one specific embodiment of the method of creating the fully-human BBB model, the cell types of step (c) are human cells.

In one specific embodiment of the method of creating the fully-human BBB model, the hPSCs are human embryonic stem cells (hESCs).

In one specific embodiment of the method of creating the fully-human BBB model, the hPSCs are induced pluripotent stem cells (iPSCs).

In one specific embodiment of the method of creating the fully-human BBB model, step (c) comprises human pericytes co-cultured with BMECs 24 hours after the purification of the BMECs. In another specific embodiment, the TEER of the confluent monolayer formed from the co-cultured BMECs and human pericytes is greater than 250 Ohm×cm².

In one specific embodiment of the method of creating the fully-human BBB model, step (c) comprises differentiated hNPCs co-cultured with BMECs 24 hours after the purification of the BMECs. In another specific embodiment, the TEER of the confluent monolayer formed from the co-cultured BMECs and differentiated hNPCs is greater than 400 Ohm×cm².

In one specific embodiment of the method of creating the fully-human BBB model, step (c) comprises human pericytes co-cultured with BMECs within 30 minutes after the purification of the BMECs. In another specific embodiment, the mixture of human pericytes and BMECs is further co-cultured with differentiated hNPCs. In yet another specific embodiment, the TEER of the confluent monolayer formed from the co-cultured BMECs, pericytes, and differentiated hNPCs is greater than 700 Ohm×cm².

In one specific embodiment of the method of creating the fully-human BBB model, after step (b) the BMECs form a monolayer wherein the cells are confluent and express an initial TEER of 35-200 Ohm×cm².

In one specific embodiment of the method of creating the fully-human BBB model, after step (c) the TEER of the confluent monolayer formed from the co-cultured BMECs and the other cell type is greater than 250 Ohm×cm².

In one embodiment, the present invention relates to a fully-human BBB model created following any of the above methods.

In one embodiment, the present invention relates to a method of creating a retinoic acid (RA)-enhanced or RA-like compound-enhanced mammalian blood-brain barrier (BBB) model, and the method comprises the steps of a) obtaining a mixture of neural cells and brain microvascular endothelial cells (BMECs) in the presence of RA or RA-like compound, wherein the mixture of neural cells and BMECs was produced from the differentiation of human pluripotent stem cells (hPSCs); b) purifying BMECs from the mixture of neural cells and BMECs; and c) co-culturing the purified BMECs with a cell type selected from the group consisting of astrocytes, pericytes and differentiated neural progenitor cells (NPCs), wherein a BBB model is created.

In one specific embodiment of the method of creating a retinoic acid (RA)-enhanced or RA-like compound-enhanced mammalian BBB model, the cell types of step (c) are human cells.

In one specific embodiment of the method of creating a retinoic acid (RA)-enhanced or RA-like compound-enhanced mammalian BBB model, the mammalian species is selected from the group consisting of rodents and primates.

In one specific embodiment of the method of creating a retinoic acid (RA)-enhanced or RA-like compound-enhanced mammalian BBB model, step (c) comprises human pericytes co-cultured with BMECs 24 hours after the purification of the BMECs. In another specific embodiment, the TEER of the confluent monolayer formed from the co-cultured BMECs and human pericytes is greater than 1500 Ohm×cm².

In one specific embodiment of the method of creating a retinoic acid (RA)-enhanced or RA-like compound-enhanced mammalian BBB model, step (c) comprises differentiated hNPCs co-cultured with BMECs 24 hours after the purification of the BMECs. In another specific embodiment, the TEER of the confluent monolayer formed from the co-cultured BMECs and differentiated hNPCs 24 hours after the purification of BMECs is greater than 2700 Ohm×cm².

In one specific embodiment of the method of creating a retinoic acid (RA)-enhanced or RA-like compound-enhanced mammalian BBB model, step (c) comprises human pericytes co-cultured with BMECs within 30 minutes after the purification of the BMECs. In another specific embodiment, the TEER of the confluent monolayer formed from the co-cultured BMECs and differentiated hNPCs within 30 minutes after the purification of BMECs, is greater than 2600 Ohm×cm².

In one specific embodiment of the method of creating a retinoic acid (RA)-enhanced or RA-like compound-enhanced mammalian BBB model, the mixture of human pericytes and BMECs is further co-cultured with differentiated hNPCs. In another specific embodiment, the TEER of the confluent monolayer formed from the co-cultured BMECs, pericytes, and differentiated hNPCs, is greater than 3300 Ohm×cm².

In one specific embodiment of the method of creating a retinoic acid (RA)-enhanced or RA-like compound-enhanced mammalian BBB model, after step (b) the BMECs form a monolayer wherein the cells are confluent and express an initial TEER greater than 1000 Ohm×cm², preferably greater than 2000 Ohm×cm².

In one specific embodiment, the present invention relates to a retinoic acid (RA)-enhanced or RA-like compound-enhanced mammalian BBB model created following any of the above methods.

In one embodiment, the present invention relates to a method of creating a retinoic acid (RA)-enhanced or RA-like compound-enhanced fully-human blood-brain barrier (BBB) model in an optimized endothelial cell medium (OECM) wherein the OECM does not contain basic fibroblast growth factor (bFGF), comprising the steps of: a) supplying a mixture of neural cells and brain microvascular endothelial cells (BMECs) in the presence of RA or RA-like compound, wherein the mixture of neural cells and BMECs was produced from the differentiation of human pluripotent stem cells (hPSCs); b) purifying BMECs from the mixture of neural cells and BMECs; and c) co-culturing the purified BMECs with a cell type selected from the group consisting of astrocytes, pericytes and differentiated NPCs in OECM.

In one specific embodiment of the method of creating a retinoic acid (RA)-enhanced or RA-like compound-enhanced mammalian BBB model in an optimized endothelial cell medium (OECM) wherein the OECM does not contain basic fibroblast growth factor (bFGF), the cell types of step (c) are human cells.

In one specific embodiment of the method of creating a retinoic acid (RA)-enhanced or RA-like compound-enhanced mammalian BBB model in an optimized endothelial cell medium (OECM) wherein the OECM does not contain basic fibroblast growth factor (bFGF), OECM contains at least 1% platelet-poor plasma-derived serum (PDS).

In one specific embodiment of the method of creating a retinoic acid (RA)-enhanced or RA-like compound-enhanced mammalian BBB model in an optimized endothelial cell medium (OECM) wherein the OECM does not contain basic fibroblast growth factor (bFGF), step (c) comprises human pericytes co-cultured with BMECs within 30 minutes after the purification of BMECs. In another specific embodiment, the TEER of the confluent monolayer formed from the co-cultured BMECs and human pericytes within 30 minutes after the purification of BMECs, is greater than 4000 Ohm×cm².

In one specific embodiment of the method of creating a retinoic acid (RA)-enhanced or RA-like compound-enhanced mammalian BBB model in an optimized endothelial cell medium (OECM) wherein the OECM does not contain basic fibroblast growth factor (bFGF), the mixture of human pericytes and BMECs is further co-cultured with differentiated hNPCs. In another specific embodiment, the TEER of the confluent monolayer formed from the co-cultured BMECs, pericytes, and differentiated hNPCs, is greater than 5000 Ohm×cm².

In one embodiment, the present invention relates to a retinoic acid (RA)-enhanced or RA-like compound-enhanced mammalian BBB model in an optimized endothelial cell medium (OECM) wherein the OECM does not contain basic fibroblast growth factor (bFGF), created following any of the above methods.

In one embodiment, the present invention relates to a blood-brain barrier (BBB) model expressing a TEER greater than 250 Ohm×cm², comprising: a) brain microvascular endothelial cells (BMECs), wherein the BMECs have been purified from a mixture of neural cells and BMECs, wherein the mixture of neural cells and BMECs was produced from the differentiation of human pluripotent stem cells (hPSCs); and b) a cell type selected from the group consisting of pericytes, astrocytes and differentiated neural progenitor cells (NPCs), wherein the cell type was co-cultured with the purified BMECs of (a) such that the purified BMECs form a monolayer wherein the cells were confluent and the TEER of the confluent monolayer may be measured at greater than 250 ohm×cm$^2$.

In one specific embodiment of the BBB model, the cell types of step (b) are human cells.

In one specific embodiment of the BBB model, step (b) comprises human pericytes co-cultured with BMECs 24 hours after the purification of BMECs and wherein the TEER of the confluent monolayer formed from the co-cultured BMECs and human pericytes is greater than 250 Ohm×cm$^2$.

In one specific embodiment of the BBB model, step (b) comprises differentiated hNPCs co-cultured with BMECs 24 hours after the purification of BMECs, wherein the TEER of the confluent monolayer formed from the co-cultured BMECs and differentiated hNPCs is greater than 400 Ohm×cm$^2$.

In one specific embodiment of the BBB model, step (b) comprises human pericytes co-cultured with BMECs within 30 minutes after the purification of BMECs.

In one specific embodiment of the BBB model, the mixture of human pericytes and BMECs is further co-cultured with differentiated hNPCs, wherein the TEER of the confluent monolayer formed from the co-cultured BMECs, pericytes, and differentiated hNPCs is greater than 700 Ohm×cm$^2$.

In one embodiment, the present invention relates to a retinoic acid (RA) or RA-like compound-enhanced mammalian blood-brain barrier (BBB) model expressing a TEER greater than 1000 Ohm×cm$^2$, comprising: a) brain microvascular endothelial cells (BMECs) wherein the BMECs have been purified from a mixture of neural cells and BMECs, wherein the mixture of neural cells and BMECs was produced from the differentiation of human pluripotent stem cells (hPSCs) in the presence of RA or RA-like compound; and b) a cell type selected from the group consisting of astrocytes, pericytes and differentiated neural progenitor cells (NPCs), wherein the cell type was co-cultured with the purified BMECs such that the purified BMECs form a monolayer wherein the cells are confluent and the TEER of the confluent monolayer may be measured at greater than 1000 Ohm×cm$^2$.

In one specific embodiment of the retinoic acid (RA) or RA-like compound-enhanced mammalian BBB model, the cell types of step (b) are human cells.

In one specific embodiment of the retinoic acid (RA) or RA-like compound-enhanced mammalian BBB model, after (a) the BMECs form a monolayer wherein the cells are confluent and express an initial TEER greater than 1000 Ohm×cm$^2$, preferably greater than 2000 Ohm×cm$^2$ [cell pop. A(RA+), FIG. 4 and cell pop. FIG. 2].

In one specific embodiment of the retinoic acid (RA) or RA-like compound-enhanced mammalian BBB model, step (b) comprises human pericytes co-cultured with BMECs 24 hours after the purification of BMECs, wherein the TEER of the confluent monolayer formed from the co-cultured BMECs and human pericytes is greater than 1500 Ohm×cm$^2$.

In one specific embodiment of the retinoic acid (RA) or RA-like compound-enhanced mammalian BBB model, step (b) comprises differentiated hNPCs co-cultured with BMECs 24 hours after the purification of BMECs, wherein the TEER of the confluent monolayer formed from the co-cultured BMECs and differentiated hNPCs is greater than 2000 Ohm×cm$^2$.

In one specific embodiment of the retinoic acid (RA) or RA-like compound-enhanced mammalian BBB model, step (b) comprises human pericytes co-cultured with BMECs within 30 minutes after the purification of BMECs. In another specific embodiment, the mixture of human pericytes and BMECs is further co-cultured with differentiated hNPCs, and wherein the TEER of the confluent monolayer formed from the co-cultured BMECs, human pericytes, and differentiated hNPCs is greater than 2000 Ohm×cm$^2$.

In one embodiment, the present invention relates to a retinoic acid (RA) or RA-like compound-enhanced mammalian blood-brain barrier (BBB) model in optimized endothelial cell medium (OECM) expressing a TEER greater than 4000 Ohm×cm$^2$, wherein the OECM does not contain basic fibroblast growth factor (bFGF), comprising: a) brain microvascular endothelial cells (BMECs) wherein BMECs have been purified from a mixture of neural cells and BMECs, wherein the mixture of neural cells and BMECs was produced from the differentiation of human pluripotent stem cells (hPSCs) in the presence of RA or RA-like compound; and b) a cell type selected from the group consisting of astrocytes, pericytes and differentiated neural progenitor cells (NPCs), wherein the cell type was co-cultured with the purified BMECs in OECM such that the purified BMECs form a monolayer wherein the cells were confluent and the TEER of the confluent monolayer may be measured at greater than 4000 Ohm×cm$^2$.

In one specific embodiment of the retinoic acid (RA) or RA-like compound-enhanced mammalian BBB model in OECM, the cell types of step (b) are human cells.

In one specific embodiment of the retinoic acid (RA) or RA-like compound-enhanced mammalian BBB model in OECM, step (b) comprises human pericytes co-cultured with the BMECs within 30 minutes after the purification of BMECs, wherein the TEER of the confluent monolayer formed from the co-cultured BMECs and human pericytes is greater than 4000 Ohm×cm$^2$.

In one specific embodiment of the retinoic acid (RA) or RA-like compound-enhanced mammalian BBB model in OECM, the mixture of human pericytes and BMECs is further co-cultured with differentiated hNPCs and wherein the TEER of the confluent monolayer formed from the co-cultured BMECs, human pericytes, and differentiated hNPCs, is greater than 5000 Ohm×cm$^2$.

In one specific embodiment of the retinoic acid (RA) or RA-like compound-enhanced mammalian BBB model in OECM, OECM contains at least 1% platelet-poor plasma-derived serum (PDS).

DESCRIPTION OF DRAWINGS

The patent or application file contains at least one drawing in color. Copies of this patent or patent application publication with color drawings will be provided by the Office upon request and payment of the necessary fee.

IMR90-4-derived BMECs were treated with RA during the EC medium treatment phase and then purified and kept in monoculture during the subculture phase. After 24 h, BMECs were transferred to medium containing 10% FBS in monoculture or co-culture with pericytes or 11-day differentiated NPCs. Pericyte co-culture elevated TEER above the monoculture control, while differentiated NPC co-culture elevated TEER further. b) IMR90-4-derived BMECs were treated with RA and then grown to confluence in the presence of pericytes during the subculture phase. The increase in baseline TEER compared to panel (a) was reproducible across six biological experiments. Medium was then changed to 10% FBS and BMECs were either kept in co-culture with the same pericytes or transferred to co-culture with 11-day differentiated hNPCs. The specific TEER increase due to differentiated hNPCs compared to pericytes is representative of three biological replicates. Statistical significance was calculated using the student's unpaired t-test. c) The optimum co-culture scheme (pericyte co-culture during the subculture phase and differentiated NPC co-culture during the co-culture phase) was assessed for seven IMR90-4 and hNPC differentiations. hNPC differentiation time ranged from 10-19 days. Each bar represents an individual biological experiment.

Figure 11:
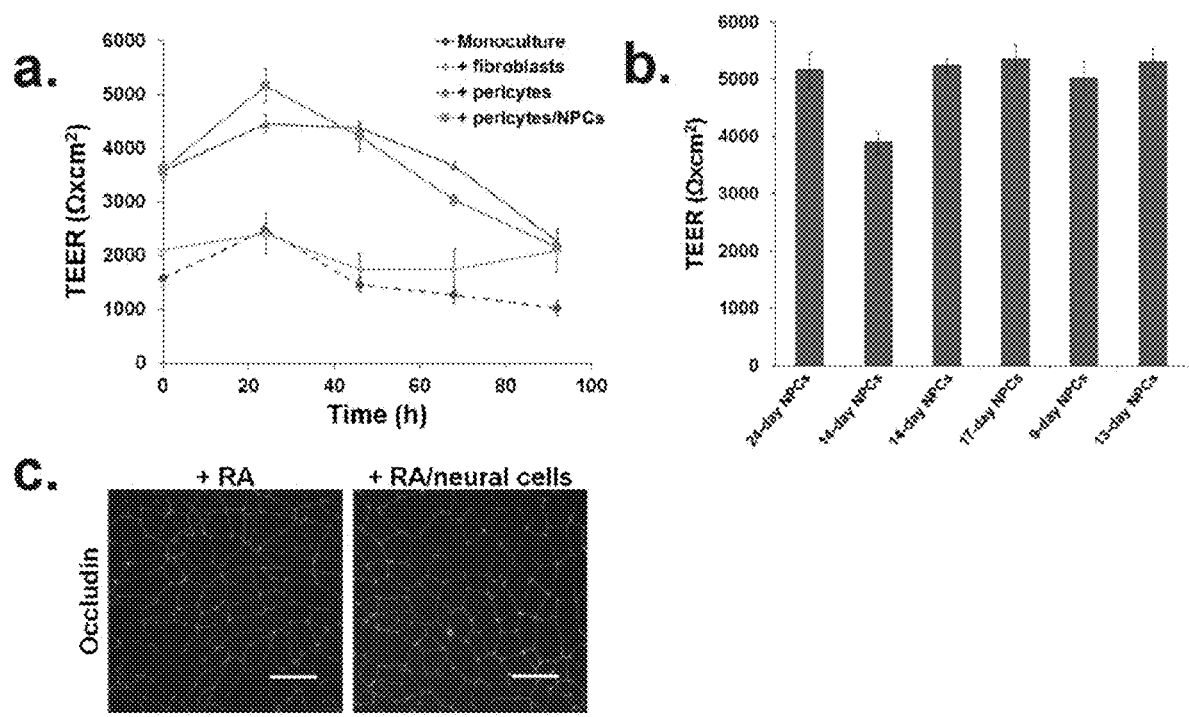

FIG. 11 is a set of diagrams showing the experimental observations of optimized co-culture in modified EC medium. a) RA-treated IMR90-4-derived BMECs were purified and maintained in monoculture or co-cultured with pericytes or fibroblasts during the subculture phase. After 24 h, the monocultured BMECs were changed to medium containing 1% PDS but lacking bFGF and RA (modified EC medium). BMECs co-cultured with fibroblasts were changed to modified EC medium. BMECs co-cultured with pericytes were either changed to modified EC medium or moved to co-culture with 14-day differentiated hNPCs in modified EC medium. The TEER increase due to pericytes relative to fibroblasts was confirmed across three biological replicates. b) RA-treated IMR90-4-derived BMECs were subcultured in the presence of pericytes and then co-cultured in modified EC medium with differentiated hNPCs ranging from 9-24 days of differentiation. Each bar represents an individual biological experiment. c) Tight junction fidelity was compared between RA-treated BMECs and RA-treated BMECs subjected to sequential co-culture with pericytes and 9-day differentiated hNPCs. Scale bars indicate 50 μm.

Figure 12:
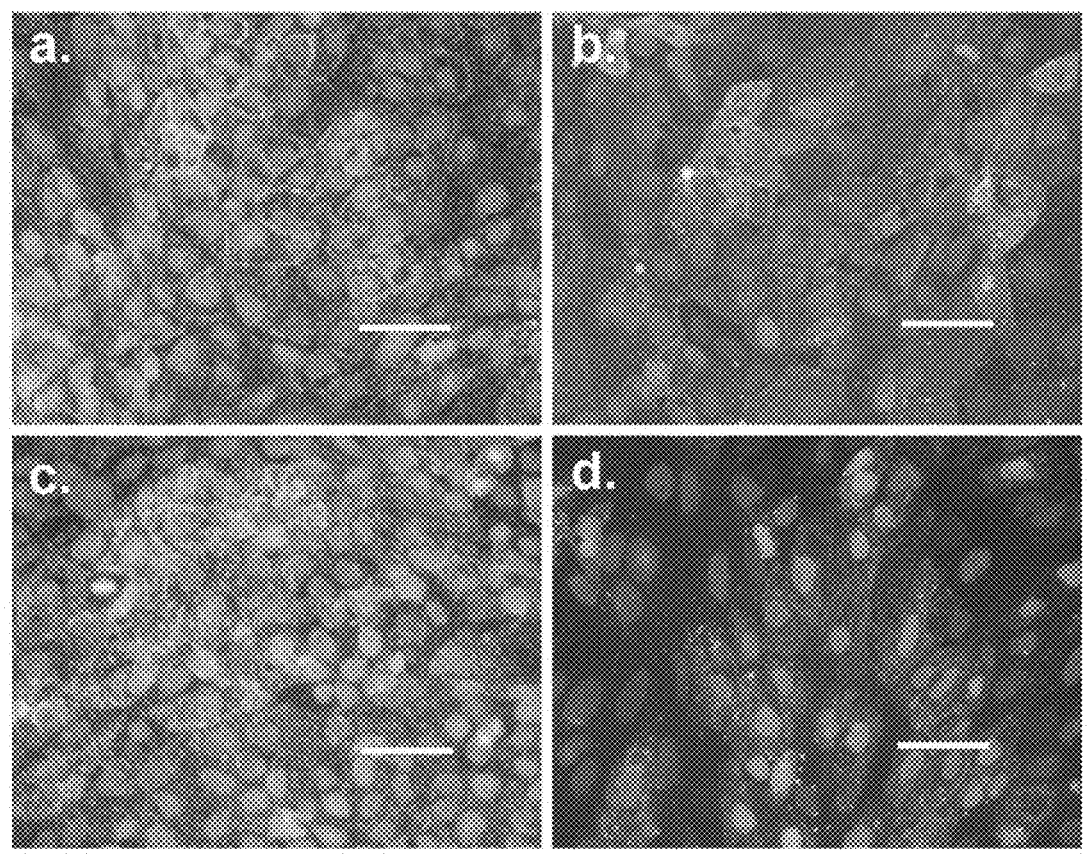

FIG. 12 is a set of pictures showing IMR90-4-derived BMECs express MRP1, BCRP, and p-glycoprotein. a) Immunocytochemical labeling of MRP1. b) Immunocytochemical labeling of BCRP. c) Immunocytochemical labeling of p-glycoprotein after cell permeabilization. d) Immunocytochemical labeling of p-glycoprotein on the cell surface only. Scale bars indicate 50 μm.

Figure 13:
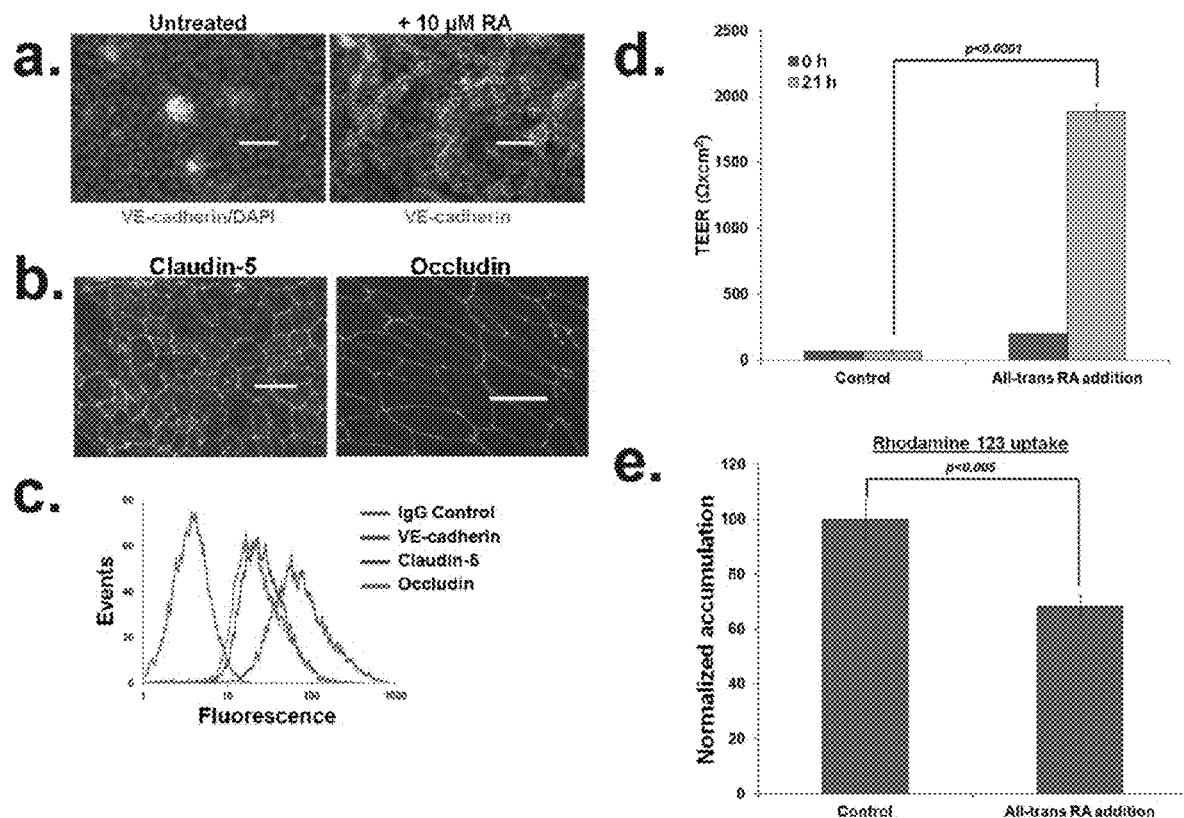

FIG. 13 is a set of diagrams showing effects of RA on DF19-9-11T-derived BMECs. a) Addition of RA during the EC medium phase induces VE-cadherin expression in DF19-9-11T iPSCs. Scale bars indicate 50 μm. (b-c) Purified DF19-9-11T-derived BMECs (assessed by flow cytometric labeling of VE-cadherin, claudin-5, and occluding) exhibit smooth and continuous junctional contacts. Scale bars indicate 50 μm. d) RA treatment increases TEER in DF19-9-11T-derived BMECs. e) RA treatment reduces accumulation of rhodamine 123 in DF19-9-11T-derived BMECs. Statistical significance was calculated using the student's unpaired t-test.

DESCRIPTION OF THE INVENTION

Fully-Human BBB

In one embodiment, the invention is a fully-human blood-brain barrier (BBB) model derived from renewable cell sources and a method of creating a fully-human BBB model. The words "fully-human blood-brain barrier" as used herein, refer to a blood-brain barrier using human cell sources. The cells are not exposed to non-human cells as the model is being prepared. In a previous US patent application (Ser. No. 13/155,435), Applicants demonstrated that human pluripotent stem cells (hPSCs) could be differentiated into brain microvascular endothelial cells (BMECs). In another previous US patent application (Ser. No. 13/218,123), Applicants demonstrated that astrocytes and neurons derived from human neural progenitor cells (hNPCs) can induce BBB properties in cultured rodent BMECs. In the present invention, the hPSC and hNPC systems are combined to create a fully-human BBB co-culture model from renewable stem cell sources.

In the present application, FIGS. 1-4 disclose that a fully-human BBB model was built in the absence of any chemical inducers (RA, etc.) by using BMECs derived from hPSCs co-cultured with pericytes or differentiated hNPCs. A RA-enhanced BBB is also disclosed. FIGS. 1-4 show differentiation and co-culture schemes for hPSC-derived BMECs. The term "subculture phase", as used herein, refers to a monoculture of hPSC-derived BMECs, or a monoculture of hPSC-derived BMECs and pericytes. The term "co-culture phase", as used herein, refers to a phase where BMECs are cultured with pericytes, differentiated hNPCs or other cell types.

Figure 1:
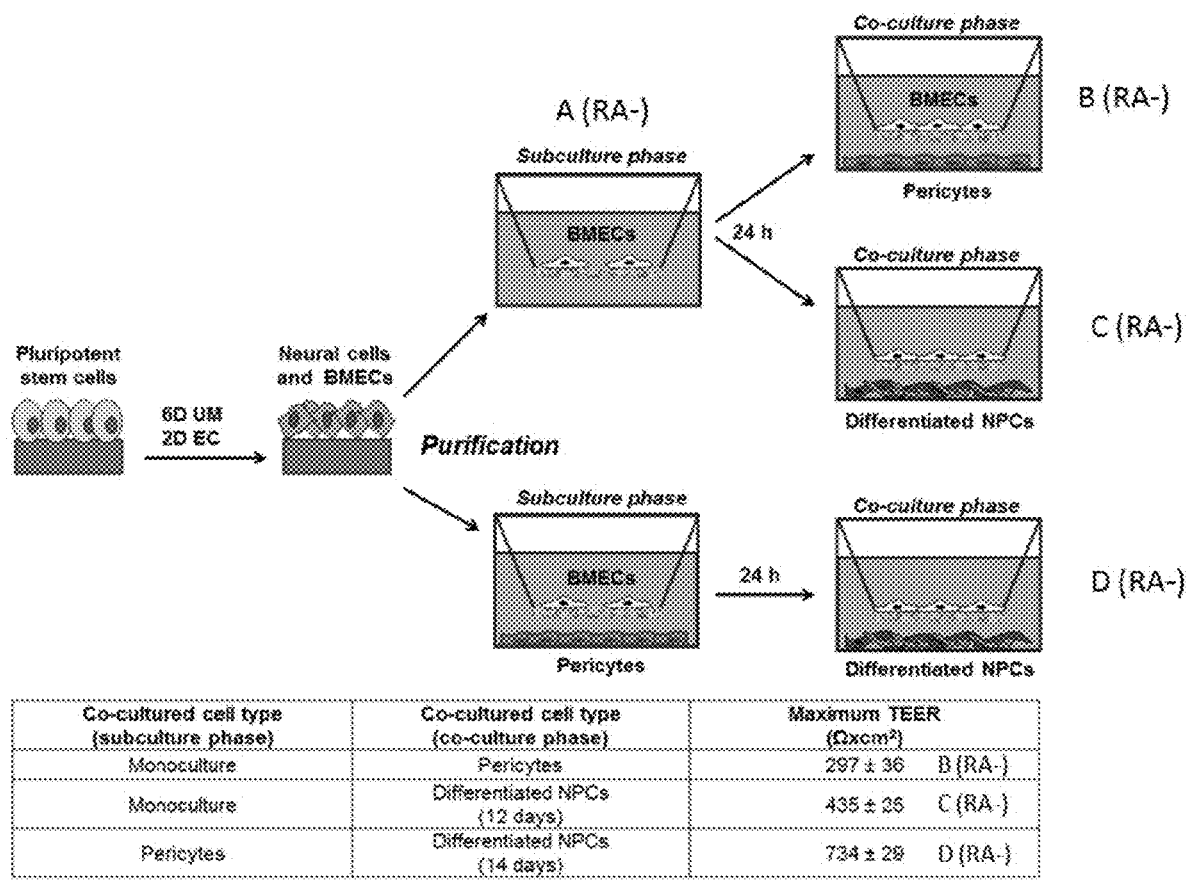
FIG. 1 is a schematic diagram showing different fully-human blood-brain barrier (BBB) models produced in the absence of retinoic acid (RA). The table shows the descriptions of physical properties of the resulting blood-brain barrier (BBB) models.

A fully-human blood brain barrier of the present invention will typically be constructed as described below. hPSCs, human pluripotent stem cells, may be obtained from many sources. The cells can include human embryonic stem cells (hESCs) or induced pluripotent stem cells (iPSCs). Preferred sources for hPSCs include those hESCs derived from blastocysts or morulas and those iPSCs reprogrammed from any somatic cell type, preferably fibroblasts. As shown in FIG. 1, hPSCs are initially subjected to 4-8 days, preferably 6 days of unconditional medium (UM) treatment, followed by 1-10 days, preferably 2-4 days of treatment with endothelial cell (EC) medium containing bFGF. A mixture of neural cells and BMECs is subsequently produced. After purification, a subculture phase of BMECs is obtained. In the absence of any further treatment, untreated IMR90-4-derived BMECs typically demonstrate baseline TEER values in the range of 50-180 $\Omega \times cm^2$ [cell population A (RA−), FIG. 1].

After 24 hours, the subculture phase of BMECs may enter a co-culture phase where BMECs were co-cultured, preferably with either pericytes [cell pop. B (RA−), FIG. 1] or 12-day differentiated hNPCs [cell pop. C (RA−), FIG. 1]. Other cell populations such as primary human astrocytes or neurons, iPSC or hESCs derived NPCs, astrocytes and neurons, etc, would also be suitable, If one does not wish to produce a fully-human culture, one may substitute cells for co-culture with other mammalian species, preferably rodent cells. In other embodiments, one may use cells from other species such as murine, bovine, porcine, and primate species. One may typically obtain suitable pericytes from commercial sources and suitable hNPCs from primary fetal tissue. hNPCS may also be purchased commercially. The 12-day differentiated hNPCs [cell pop. C (RA−), FIG. 1] can induce a higher resistance with a measured TEER of 435±25 $\Omega \times cm^2$, than pericytes [cell pop. B (RA−), FIG. 1], which show a TEER of 297±36 $\Omega \times cm^2$.

To test whether pericytes could "prime" the hPSC-derived BMECs and to better understand the function of pericytes during the phases of subculture and co-culture, hPSC-derived BMECs were co-cultured with pericytes immediately (within 30 minutes) after the purification process (FIG. 1). After 24 hours of the subculture phase of BMECs with pericytes, the BMECs were then co-cultured with differentiated hNPCs [cell pop. D (RA), FIG. 1]. The step for producing the cell population of D (RA−) as shown in FIG. 1, also called a "sequential co-cultured process," produced the highest TEER of 734±29 Ω×cm$^2$ as compared with either pericytes alone [cell pop. B (RA−), FIG. 1] or 12-days differentiated hNPCs alone [cell pop. C (RA−), FIG. 1].

RA-Enhanced BBB

In another embodiment, the invention is a retinoic acid (RA)-enhanced mammalian BBB model and a method of creating an RA-enhanced BBB model. The mammalian species is preferably selected from the group consisting of murine, bovine, porcine, and primate species. A murine species is preferably a rat, and a primate is preferably a human. As shown in FIGS. 2-5 and 7-13, the present invention discloses that a RA-enhanced mammalian BBB model was built in the presence of chemical inducers (RA or RA-like compounds) by using BMECs derived from hPSCs co-cultured with pericytes, astrocytes, or differentiated neural progenitor cells (NPCs). BMECs were produced and purified from hPSCs using the same protocol as described in fully-human BBB models.

Further, Applicants tested a list of compounds for the ability to mimic the activity of RA. The compounds found not to induce elevated TEER in the iPSC-derived BMECs included BMS 453 (RARβ agonist), 6-formylindolo[3,2-B] carbazole (AHR agonist), CITCO (CAR agonist), pregnenolone-16α-carbonitrile (PXR/SXR agonist), 3,5-diiodo-L-thyronine (THR agonist), docosa-4Z,7Z,10Z,13Z,16Z,19Z-hexaenoic acid (RXR/FXR agonist), 25-hydroxyvitamin D3 (VDR agonist), WY-14643 (PPARα agonist), 5,8,11,14-eicosatetraynoic acid (PPARα agonist), ciglitazone (PPARγ agonist), paxilline (LXR agonist), 3,5-diiodo-4-hydroxyphenylpropionic acid (THR agonist), cholic acid (FXR agonist), rifampicin (PXR agonist), and others.

The compounds found to induce elevated TEER in the iPSC-derived BMECs comprised CD 3254 (RXRα agonist), BMS 753 (RARα agonist), and carbacyclin (PPARβ/δ agonist).

In the present invention, Applicants define "RA-like compounds" to include CD 3254 (RXRα agonist), BMS 753 (RARα agonist), and carbacyclin (PPARβ/δ agonist). Applicants envision that RA-like compounds can substitute for RA in the methods described above and below.

All-trans RA was chosen as a potential candidate to improve BBB characteristics as the BBB has been shown to express retinol-binding proteins and its membrane receptor STRA6, and all-trans RA has been shown to upregulate certain BBB properties in immortalized rodent BMEC lines. Additionally, RA signaling may be upregulated in the BBB.

A typical retinoic acid-enhanced blood brain barrier is created as described below and in the figures. Retinoic acid suitable for the present invention may be obtained from commercial sources such as Sigma-Aldrich. Applicants tested two isoforms of RA, including all-trans and 9-cis, with both all-trans and 9-cis isoforms producing the desired enhancement. Both types of RA are suitable for the present invention.

Figure 2:
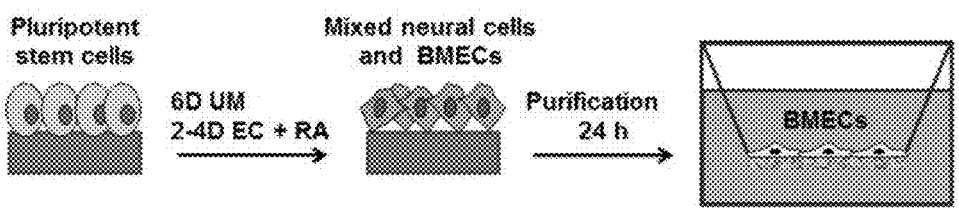
FIG. 2 is a schematic diagram showing one example of BBB models produced before the co-culture phase in the presence of retinoic acid (RA). The table shows the descriptions of physical properties of the resulting BBB model.
Figure 3:
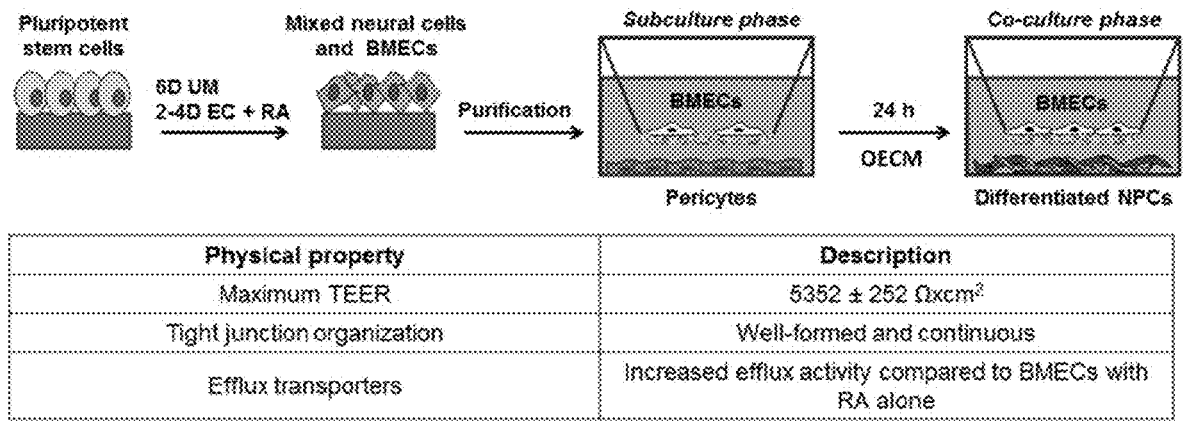
FIG. 3 is a schematic diagram showing one of the optimized BBB models produced after the co-culture phase in the presence of retinoic acid (RA) and optimized EC medium (OECM). The table shows the descriptions of physical properties of the resulting BBB model.
Figure 4:
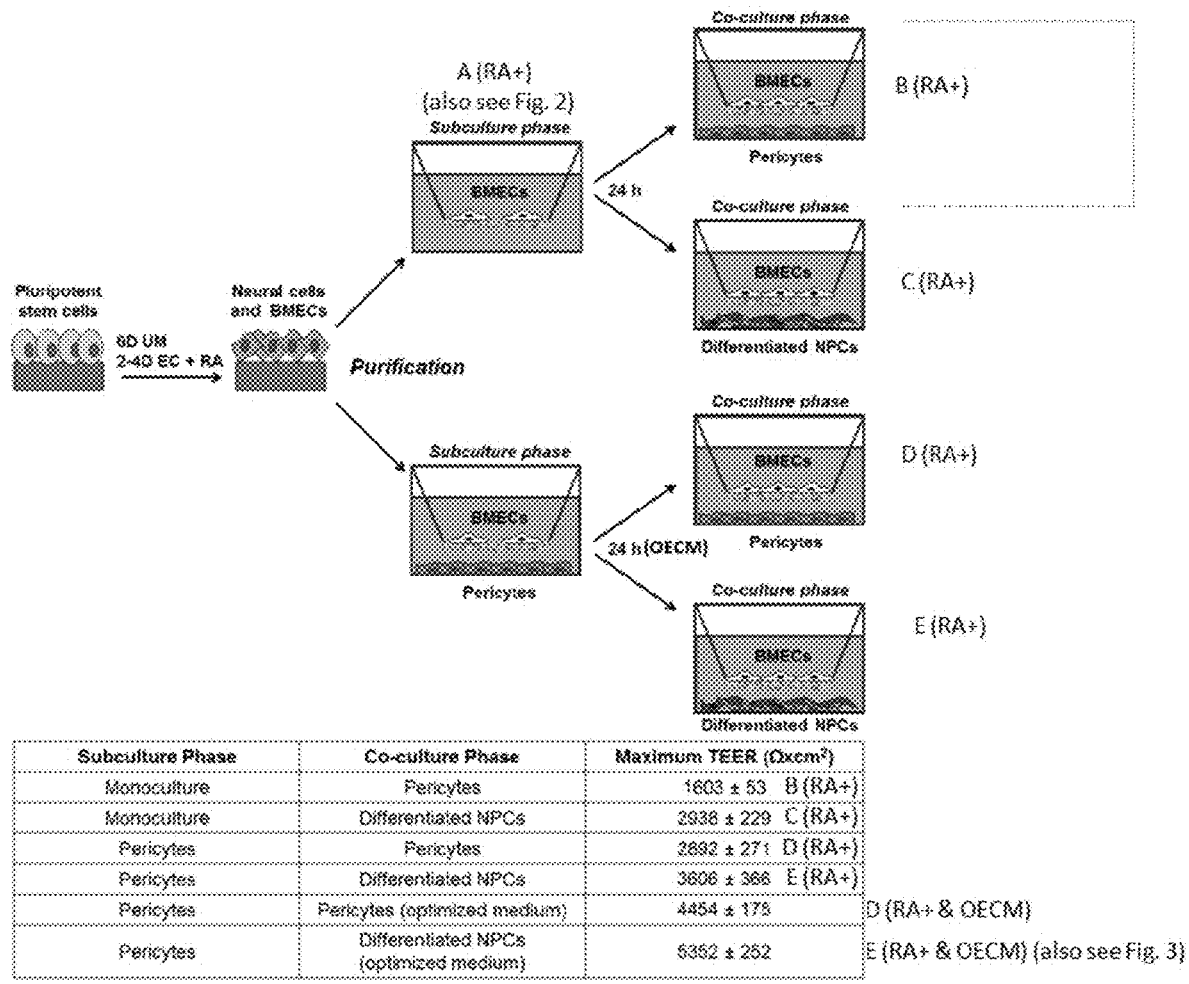
FIG. 4 is a schematic diagram showing different blood-brain barrier (BBB) models produced in the presence of retinoic acid (RA). The table shows the descriptions of physical properties of the resulting BBB models. hPSCs are subjected to 6 days of unconditioned medium (UM) treatment, followed by 2-4 days of treatment with endothelial cell (EC) medium containing bFGF with retinoic acid (RA), which yields a mixture of neural endothelial cells. Timing of RA addition is cell line-dependent and described in the Results section. hPSC-derived BMECs are then purified onto filters in EC medium containing bFGF with RA. For Schemes B and C, BMECs are allowed to reach confluence in monoculture (denoted the subculture phase). For Schemes D and E, BMECs are allowed to reach confluence in the presence of pericytes. After 24 h in the subculture phase, BMECs are then co-cultured with pericytes or differentiated hNPCs (denoted the co-culture phase) in medium containing 10% fetal bovine serum (FBS; see the Example) or EC medium without bFGF or RA (modified EC medium). The start of the co-culture phase is defined as time t=0 h in all TEER plots throughout the specification. Human foreskin fibroblasts were used during the subculture and co-culture phases in certain experiments as a non-neural cell control.

In a typical embodiment of the present invention, IMR90-4 induced pluripotent stem cells (IPSCs) are first differentiated for 4-8 days, preferably 6 days, in a standard unconditioned medium (UM) and for 1-10 days, preferably 2-4 days, in EC medium to generate a mixed population of neural cells and BMECs. IMR90-4 denotes the cells which the iPSCs were derived from—the IMR90 fibroblast line—and "4" indicates a particular clone from the derivation process. Other cell lines are also suitable. RA is added during the 1-5 days, preferably 2 days of the EC medium treatment (FIGS. 2-4). To yield the desired response, the overall concentration of RA was in the range of 2-20 μM, preferably 2-10 μM.

After 24 hours, the subculture phase of BMECs may enter a co-culture phase where BMECs were co-cultured, preferably with either pericytes [cell pop. B (RA+), FIG. 4] or 12-day differentiated hNPCs [cell pop. C (RA+), FIG. 4]. Other cell populations would also be suitable, such as primary human astrocytes or neurons, iPSC or hESCs derived NPCs, astrocytes and neurons, rodent NPCs, primary rodent astrocytes, rodent pericytes, etc. In other embodiments, one may use cells derived from other species such as murine, bovine, porcine, and primate species.

The enhancement effect of RA was investigated by analyzing adherens junction and tight junction protein expression. Immunocytochemistry studies demonstrated that addition of 10 μM RA could induce significant VE-cadherin expression whereas 1 μM RA could not (FIG. 7a). The number of cells with elevated GLUT-1 expression determined by flow cytometry remained unchanged following the RA treatment (FIG. 7b). However, following RA treatment the level of occludin expression increased by 1.8 to 2.9 fold and the level of claudin-5 expression decreased by 1.7 fold. These observations were further confirmed by the western blot analysis (FIG. 7c-d). As determined by immunocytochemistry analysis of PECAM-1 expression, the total number of ECs in culture remained unchanged following the RA treatment, indicating the observed increases in protein expression could be correlated to the endothelium.

Further, both untreated IMR90-4-derived BMECs as a control experiment and RA-treated IMR90-4-derived BMECs were purified by matrix adhesion on either polystyrene plates or TRANSWELL filters and the resulting BMECs were allowed to grow to confluence. Immunocytochemistry analysis demonstrated that untreated IMR90-4-derived BMECs possessed a significant number of discontinuous tight junction strands with frayed edges (12.7±7.1%), while RA-treated IMR90-4-derived BMECs maintained mostly smooth junctions (1.5±0.9%) (FIG. 8b). To further correlate the observations of Immunocytochemistry analysis with physical barrier properties, TEER measurements were conducted on both untreated and RA-treated IMR90-4-derived BMECs. While untreated IMR90-4-derived BMECs showed baseline TEER values in the range of 50-180 Ω×cm$^2$, RA-treated IMR90-4-derived BMECs demonstrated significantly elevated baseline TEER in the range of 300-1500 Ω×cm$^2$ ([t=0 h]; t=0 refers to 24 hours after purification when BMECs have just reached confluence.) (FIG. 8c and Table 1).

TABLE 1

Effect of RA treatment on TEER.

| Treatment | Biological Replicates | Average TEER ($\Omega \times cm^2$) | Maximum TEER ($\Omega \times cm^2$) |
|---|---|---|---|
| IMR90-4-derived BMECs (t = 0 h) | | | |
| Untreated | N = 5 | 101 ± 47 | N.A. |
| +RA | N = 13 | 956 ± 345 | 1502 ± 145 |

TABLE 1-continued

Effect of RA treatment on TEER.

| Treatment | Biological Replicates | Average TEER ($\Omega \times cm^2$) | Maximum TEER ($\Omega \times cm^2$) |
|---|---|---|---|
| IMR90-4-derived BMECs (t = 24 h) | | | |
| Untreated | N = 3 | 228 ± 57 | N.A. |
| +RA | N = 12 | 2935 ± 802 | 3674 ± 367 |
| DF19-9-11 T-derived BMECs (t = 24 h) | | | |
| +RA | N = 2 | 1707 ± 417 | 1968 ± 288 |
| H9-derived BMECs (t = 24 h) | | | |
| +RA | N = 4 | 646 ± 308 | 1028 ± 153 |

Average TEER values are presented as mean ± S.D. between biological replicates whereas maximum TEER values are presented as mean ± S.D. between triplicate filters.

After the initial TEER measurements, both untreated and RA-treated IMR90-4-derived BMECs may be transferred to an optimized EC medium (OECM) (FIG. 4). The OECM does not include bFGF or RA, and the OECM includes at least 1% platelet-poor plasma-derived serum (PDS). TEER measurements re-taken after 24 hours typically demonstrate that RA-treated IMR90-4-derived BMECs demonstrate consistently increased TEER above 2000 $\Omega \times cm^2$ and often exceeding 3000 $\Omega \times cm^2$, whereas untreated BMECs rarely exhibit TEER above 300 $\Omega \times cm^2$ (FIG. 8c). These observations indicate a significant contribution of RA to the passive barrier of IMR90-4-derived BMECs.

In one embodiment, the present invention is an optimization of a mammalian RA-enhanced BBB model by co-culturing BMECs with pericytes or differentiated NPCs and a method of creating an optimized BBB model. Enlightened by the fully-human BBB model discussed above which used BMECs derived from hPSCs co-cultured with pericytes or differentiated hNPCs, Applicants further attempted to optimize the human co-culture BBB model by co-culturing RA-treated IMR90-4-derived BMECs with pericytes [cell pop. B (RA+), FIG. 4] or differentiated hNPCs [cell pop. C (RA+), FIG. 4]. In the presence of RA, BMECs produced from the monoculture experiment [cell pop. A (RA+), FIG. 4] typically express a TEER in the range of 1000-4000 $\Omega \times cm^2$, preferably at least 2935±802 $\Omega \times cm^2$ (FIG. 2). Co-culture of RA-treated IMR90-4-derived BMECs with pericytes in the co-culture phase [cell pop. B (RA+), FIG. 4] creates a TEER of at least 1603±53 $\Omega \times cm^2$ as compared with the corresponding monoculture experiment which produced a TEER of at least 1043±107 $\Omega \times cm^2$ [cell pop. A (RA+), FIG. 4; FIG. 10a and Table 2; p<0.002], demonstrating a significant increase of the barrier property. Further, co-culture with differentiated hNPCs [cell pop. C (RA+), FIG. 4] increased the barrier property even more significantly with a TEER of at least 2367±116 $\Omega \times cm^2$ (FIG. 10a; p<0.001).

TABLE 2

Maximum TEER achieved using neural cell co-cultures.

| Co-cultured cell type (subculture phase) | Co-cultured cell type (co-culture phase) | Co-culture medium[a] | Maximum TEER ($\Omega \times cm^2$)[b] |
|---|---|---|---|
| IMR90-4-derived BMECs | | | |
| Monoculture | Monoculture | 10% FBS | 1044 ± 107 |
| Monoculture | Pericytes | 10% FBS | 1603 ± 53 |
| Monoculture | Differentiated NPCs (10 days) | 10% FBS | 2938 ± 229 (3) |
| Pericytes | Pericytes | 10% FBS | 2892 ± 271 |
| Pericytes | Differentiated NPCs (10 days) | 10% FBS | 3606 ± 366 (7) |
| Pericytes | Pericytes | 1% PDS | 4454 ± 175 |
| Pericytes | Differentiated NPCs (17 days) | 1% PDS | 5352 ± 252 (6) |
| DF19-9-11T-derived BMECs | | | |
| Pericytes | Differentiated NPCs (11 days) | 1% PDS | 4738 ± 303 (2) |
| H9-derived BMECs | | | |
| Pericytes | Differentiated NPCs (9 days) | 1% PDS | 1675 ± 95 (2) |

The subculture phase and co-culture phase are described in FIG. 1. RA was used in all experiments.
[a]Refers to the serum component of the co-culture medium (see Materials and Methods for further descriptions).
[b]Maximum TEER was typically observed 24 h after initiation of the co-culture phase. The number in parenthesis indicates how many times the optimum condition for each co-culture experiment was tested. Mean ± S.D. was calculated from at least three filters per experiment.

Figure 10:
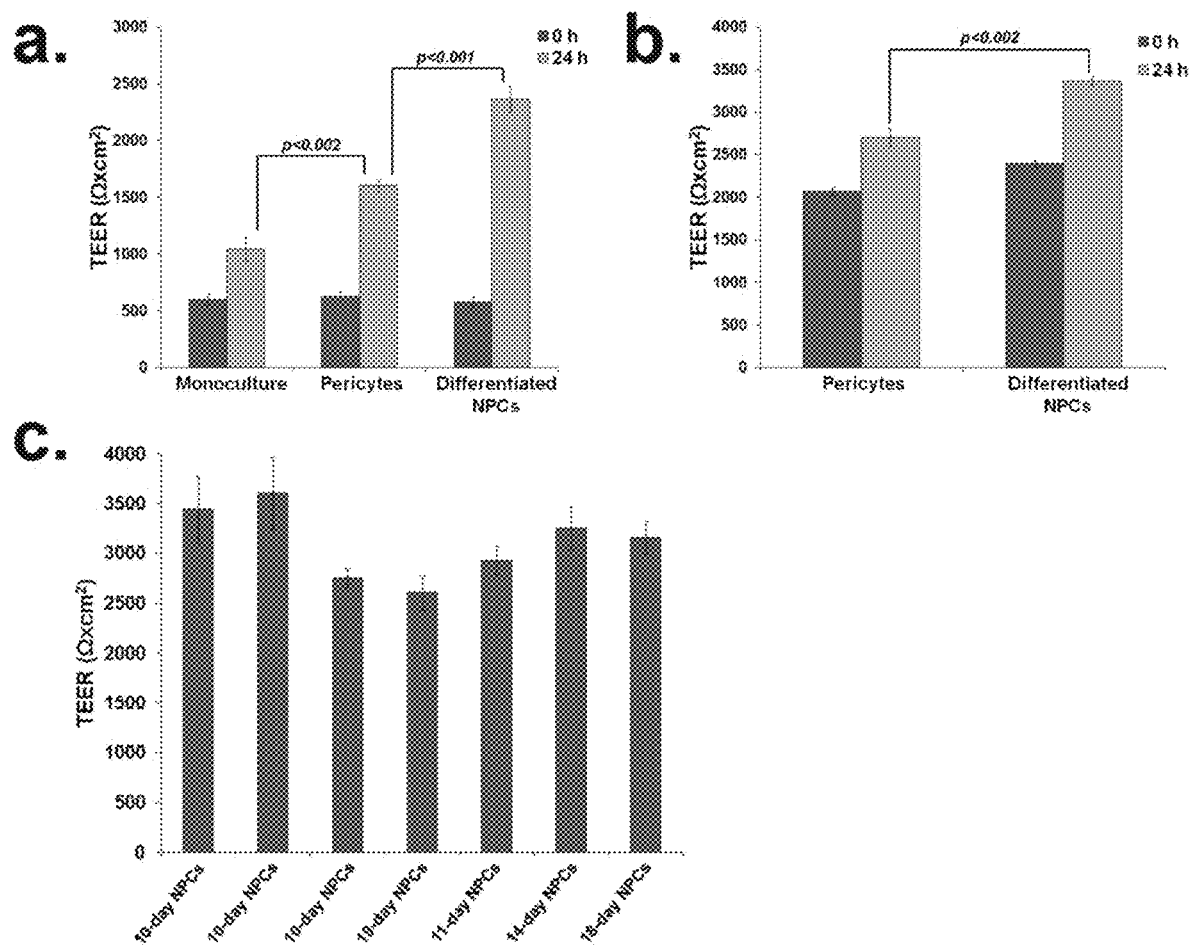
FIG. 10 is a set of diagrams showing that RA enhances the effects of pericyte and differentiated hNPC co-culture. a)

Moreover, when pericytes are added to RA-treated BMECs during the subculture phase [cell pop. D (RA+) and E (RA+), FIG. 4], the barrier property at confluence is significantly enhanced with a TEER of at least 2068±124 $\Omega \times cm^2$ as compared to the monoculture BMECs having a TEER of at least 579±42 $\Omega \times cm^2$ (FIG. 10b and FIG. 10a; p<0.0001). These BMECs, which were initially co-cultured with pericytes, were then co-cultured with differentiated hNPCs [cell pop. E (RA+), FIG. 4], leading to a further enhanced TEER of at least 3370±152 $\Omega \times cm^2$ (FIG. 10). As comparison, if the same BMECs remained co-cultured with pericytes, the resulting TEER is at least 2701±53 $\Omega \times cm^2$, showing less significant increase as that co-cultured with differentiated hNPCs (FIG. 10b). These observations confirmed that a sequential pericyte/hNPC co-culture is the optimized condition for increasing barrier properties. Even with the variability in age and differentiation time among the three cell types (IMR90-4 iPSCs, pericytes, and hNPCs), this model proves extremely reproducible (Table 2).

In another embodiment, the invention is the optimization of a human BBB model in an optimized EC medium (OECM). The experiments with RA treatment alone demonstrated a significant increase of TEER in a medium containing at least 1% platelet-poor plasma-derived serum (PDS) after basic fibroblast growth factor (bFGF) had been removed (FIG. 8c), also termed as an optimized EC medium. Thus, in Exhibit A we conducted an experiment of sequential pericyte/hNPC co-culture [cell pop. D (RA+ & OECM), FIG. 4] in an optimized EC medium to further optimize the barrier property of the resulting BBB. In an optimized EC medium, the barrier property was further increased as compared with the medium containing 10% FBS which was used in the experiments of paragraphs 27 and 28 (FIG. 11). For example, RA-treated IMR90-4-derived BMECs co-cultured with pericytes during the subculture phase showed a significantly enhanced TEER of 3573±175 $\Omega \times cm^2$ in the optimized EC medium as compared with that in the medium containing 10% FBS, having a TEER of 1575±163 $\Omega \times cm^2$ (FIG. 11a [t=0]; p<0.0001). In the absence of pericytes, RA-treated IMR90-4-derived BMECs showed a less significantly enhanced TEER of 2106±30 $\Omega \times cm^2$ in the optimized EC medium as compared with that in the medium containing 10% FBS.

Further, in the optimized EC medium, the measured TEER in the monoculture experiments remained relatively unchanged after 24 hours (FIG. 11a). In contrast, the co-cultured experiments with pericytes further increased TEER to 4454±174 $\Omega \times cm^2$ after 24 hours and the experiments of sequential pericyte/hNPC co-culture yielded even higher TEER of 5160±318 $\Omega \times cm^2$ after 24 hours [cell pop. D (RA+ & OECM), FIG. 4; FIG. 11a; p<0.05].

Under the optimized conditions, including a sequential pericyte/hNPC co-culture in the optimized EC medium (OECM), the models of RA-treated hPSC-derived BMECs achieved consistently elevated TEERs with different hPSC cell lines. For example, the application of H9-derived BMECs led to a TEER of 1675±95 $\Omega \times cm^2$, the use of DF19-9-11T-derived BMECs led to a TEER of 4738±303 $\Omega \times cm^2$, and IMR90-4-derived BMECs produced a TEER of 5352±252 $\Omega \times cm^2$.

The invention of the hPSC-derived BMECs pericyte and/or differentiated hNPC system represents the first BBB model constructed from renewable sources. Pericytes share the basement membrane with endothelial cells in capillaries and play important roles in endothelial maturation and survival, as well as specific roles in BBB development. It has been previously shown that pericytes can be cultured for twenty weeks with over forty population doublings (Crisan, M. et al., 2008), indicating that pericytes may potentially be derived from a small primary source and expanded significantly. The fetal brain pericytes used in the current study were purchased commercially and one vial was expanded in quantities large enough to conduct all experiments discussed herein. Further, hNPCs, derived from primary fetal tissue, have long been recognized for their extensive self-renewal capabilities (Wright, L. S. et al., 2003). Thus, hNPCs can be expanded as an unlimited supply of neural cells. Moreover, the rapidly-expanding field of hPSC technology is likely to eventually make these primary sources unnecessary.

The present invention represents the first human in vitro BBB model and benchmarks the most significant barrier properties which are unmatched by any previous in vitro models. The combination of RA treatment with pericytes and differentiated hNPC co-culture resulted in hPSC-derived BMECs demonstrating the maximum TEER in excess of 5000 $\Omega \times cm^2$. Such TEERs are several fold higher than the closest animal model and more than 10-fold higher than any published human model (Deli, M. A., et al., 2005). Further, the results of TEERs were compared with those measured in in vivo experiments. Classic experiments performed by Crone and Olesen (Crone, C. and Olesen, S. P., 1982) showed an average TEER of 1870 $\Omega \times cm^2$ in the frog BBB, while experiments on the brains of maturing rats (above 21 days of gestation) by Butt and co-workers (Butt, A. M., et al., 1990) yielded an average TEER of 1490±170 $\Omega \times cm^2$ in brain arterial vessels and 918±127 $\Omega \times cm^2$ in venous vessels. Both sets of experiments appear well below the level of TEER achieved in the current study.

However, Crone and Olesen (Crone, C. and Olesen, S. P., 1982) described a maximum TEER value of 2976 $\Omega \times cm^2$ in the frog BBB, and they speculated that one might expect a maximum TEER of 4000 $\Omega \times cm^2$ on the basis of their theoretically calculated value of conductance. Similarly, Butt and co-workers (Butt, A. M., et al., 1990) demonstrated a maximum value of 5900 $\Omega \times cm^2$ in the rat brain, and they further stated that "any potential deterioration of the preparation would tend to lower the measured values, so it is conceivable that the higher figures reflect the true resistance of the blood-brain barrier". Moreover, a separate study by Smith and Rapoport (Smith, Q. R. and Rapoport, S. I, 1986.) estimated an in vivo TEER of 8000 $\Omega \times cm^2$ at the rat BBB on the basis of their measured permeability coefficients of radioisotopic ions. Thus, the TEER achieved by the BBB model is not beyond the measured or predicted range of in vivo TEER and it is in fact as close to an in vivo barrier as have ever been measured in an in vitro model.

EXAMPLES

Materials and Methods hPSC Differentiation to BMECs.

IMR90-4 and DF19-9-11T hiPSCs and H9 hESCs were maintained between passages 26-42 on MATRIGEL (BD Biosciences) in mTeSR1™ medium (STEMCELL Technologies) or on irradiated mouse embryonic fibroblasts (MEFs) in standard unconditioned medium (Dulbecco's Modified Eagle's Medium [DMEM]/Ham's F12 containing 20% Knockout Serum Replacer (Invitrogen), 1×MEM non-essential amino acids (Invitrogen), 1 mM L-glutamine (Sigma), 0.1 mM β-mercaptoethanol (Sigma), and human basic fibroblast growth factor (bFGF; 100 ng/mL for hiPSCs and 4 ng/mL for hESCs; Waisman Clinical Biomanufacturing Facility, University of Wisconsin-Madison)). Prior to differentiation, cells were passaged onto Matrigel (BD Biosciences) in mTeSR1 medium (STEMCELL Technologies). After 2-3 days in mTeSR1, medium was switched to unconditioned medium (UM) lacking bFGF for 6 days. Human endothelial serum-free medium (hESFM; Invitrogen) supplemented with 20 ng/mL bFGF (R&D Systems) and 1% platelet-poor plasma derived bovine serum (Biomedical Technologies, Inc.) was then added for an additional 2-4 days.

All-trans RA (Sigma) was included at concentrations of 1-10 µM depending on the experiment. Equivalent DMSO was used as a vehicle control in some experiments. Cells were then dissociated with Versene (Invitrogen) and plated onto 12-well tissue culture polystyrene plates or 1.12 $cm^2$ Transwell-Clear® permeable inserts (0.4 µm pore size) coated with a mixture of collagen IV (400 µg/mL; Sigma) and fibronectin (100 µg/mL; Sigma). Culture plates were incubated with the coating for at least 30 min at 37° C., while the inserts were incubated for a minimum of 4 h at 37° C. hPSC-derived BMECs were then cultured in EC medium overnight (with or without RA). Our previous hPSC differentiation protocol utilized dispase for purifying the BMECs, but we have qualitatively observed that non-enzymatic treatment of the BMECs with EDTA resulted in less debris attached to the purified monolayer and have thus switched to Versene for all subculture of BMECs. Also, our previous study used hPSCs exclusively maintained on MEFs. In this study, no noticeable differences in BBB properties were observed between hPSCs maintained on MEFs and hPSCs maintained under feeder-independent conditions.

Primary Cell Culture: Human Neural Progenitor Cells, Human Pericytes, and Human Foreskin Fibroblasts Human neural progenitor cells (hNPCs) were obtained as previously described (Lippmann, et al., 2011). hNPCs were maintained in NPC culture medium (70%:30% DMEM/F12 (Sigma/Invitrogen) supplemented with 2% B27 (Invitrogen), 1% antibiotic-antimycotic (Invitrogen), 20 ng/mL bFGF, 20 ng/mL epidermal growth factor (EGF; Sigma), 10 ng/mL leukemia inhibitory factor (LIF; Millipore, Billerica, Mass., USA), and 5 µg/mL heparin (Sigma)), and cells were passaged every 7-10 days using standard chopping methods. To initiate differentiation, NPCs were dissociated with ACCUTASE (Invitrogen) and seeded onto 12-well plates or filters coated with poly-L-lysine/laminin (Sigma) at a density of $2\times10^5$ cells/well or $5\times10^4$ cells/filter. Differentiation medium consisted of NPC maintenance medium with the growth factors replaced by 1% fetal bovine serum (FBS; Invitrogen). Medium was changed every third day. NPCs were differentiated 9-24 days prior to use in co-culture experiments, as indicated in the Results section.

Primary human brain pericytes derived from fetal tissue were purchased commercially (Sciencell, San Diego, Calif., USA). These cells possessed uniform expression of nestin and platelet-derived growth factor receptor-β and heterogeneous expression of α-smooth muscle actin (data not shown). They were maintained in DMEM supplemented with 10% FBS, and expanded for two passages, upon which stock vials were frozen in liquid nitrogen. Pericytes were then utilized from the original cell culture, or from thawed stock vials, between passages 2-12. Medium was changed every second day and cells were subcultured after reaching ~90% confluency. For subculture, pericytes were washed once with PBS and incubated with ACCUTASE for 5-10 min until cells began to detach. Pericytes were re-seeded at a density of $5\times10^3$ cells/cm$^2$ on poly-L-lysine-coated flasks or plates. Pericytes were seeded in 12-well plates 1-2 days prior to co-culture and typically were 50-80% confluent when co-culture was initiated. Primary human foreskin fibroblasts (BJ line; ATCC) were cultured in Minimum Essential Medium (Sigma) supplemented in 10% FBS and used as a negative control in certain co-culture experiments.

Initiation of Co-Culture Experiments

Figure 5:
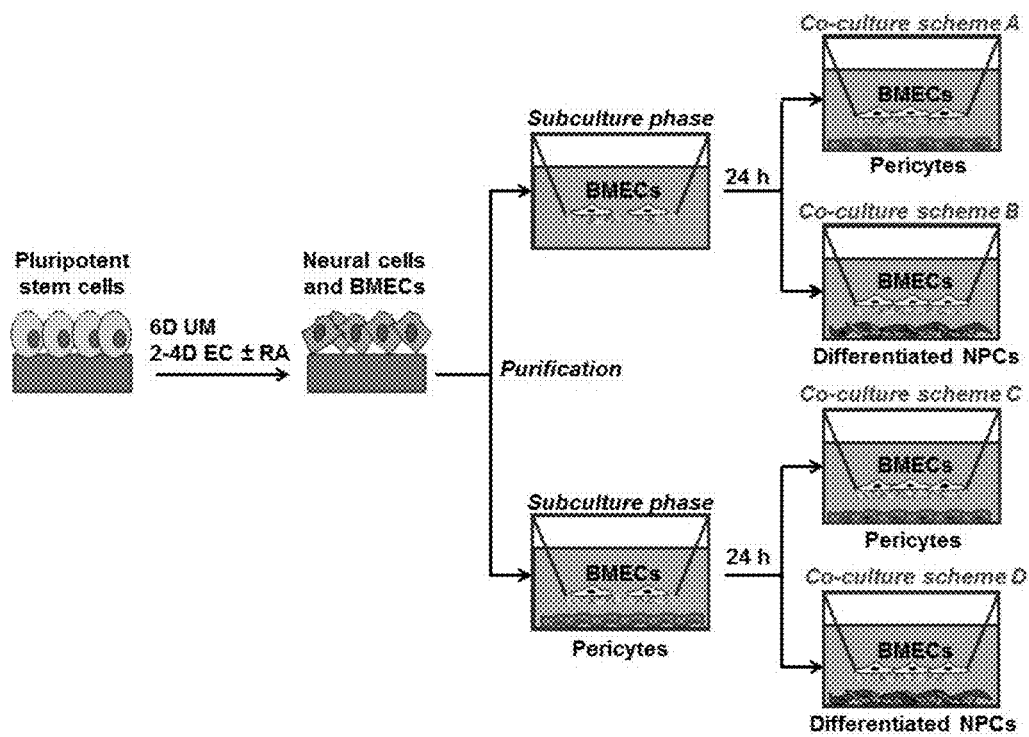
FIG. 5 is a schematic diagram showing differentiation and co-culture schemes for hPSC-derived BMECs. hPSCs are subjected to 6 days of unconditioned medium (UM) treatment, followed by 2-4 days of treatment with endothelial cell (EC) medium containing bFGF with or without retinoic acid (RA), which yields a mixture of neural endothelial cells. Timing of RA addition is cell line-dependent and described in the Results section. hPSC-derived BMECs are then purified onto filters in EC medium containing bFGF with or without RA. For Schemes A and B, BMECs are allowed to reach confluence in monoculture (denoted the subculture phase). For Schemes C and D, BMECs are allowed to reach confluence in the presence of pericytes. After 24 h in the subculture phase, BMECs are then co-cultured with pericytes or differentiated hNPCs (denoted the co-culture phase) in medium containing 10% FBS (defined in Materials and Methods section) or EC medium without bFGF or RA (modified EC medium). The start of the co-culture phase is defined as time t=0 h in all TEER plots throughout the manuscript. Human foreskin fibroblasts were used during the subculture and co-culture phases in certain experiments as a non-neural cell control.

FIG. 5 dictates the timing of co-culture experiments. During the subculture phase, hPSC-derived BMECs were monocultured or co-cultured with pericytes or fibroblasts in EC medium (with or without RA). After the 24 h subculture phase, hPSC-derived BMECs were maintained as a monoculture or co-cultured with differentiated hNPCs, pericytes, or fibroblasts. Depending on the experiment, co-culture was conducted in NPC differentiation medium containing 10% FBS (as opposed to the 1% FBS used during NPC differentiation) or hESFM containing 1% PDS but not bFGF (modified EC medium). Trans-endothelial electrical resistance (TEER) was measured immediately prior to co-culture using an EVOM voltohmmeter (World Precision Instruments, Sarasota, Fla., USA) and approximately every 24 h thereafter as necessary.

Immunocytochemistry and Analysis of Tight Junction Fidelity

Cells were washed twice with phosphate-buffered saline (PBS; Sigma) and fixed with either 100% ice-cold methanol for 10 min or 4% paraformaldehyde for 15 min. Cells were then washed twice with PBS and blocked in PBS containing 40% goat serum (40% PBSG; Sigma) at 20° C. for 30 min. In some instances, 0.1% Triton X-100 (TX-100) was included during this step to permeabilize the cells. Cells were then washed once with PBS and incubated with primary antibodies against occludin (1:100; Invitrogen), claudin-5 (1:100; Invitrogen), VE-cadherin (1:25; Santa Cruz Biotechnology), von Willebrand Factor (vWF; 1:100; Dako), p-glycoprotein (clone F4; 1:25; Lab Vision), breast cancer resistance protein (BCRP, clone 5D3; 1:25; Millipore), multidrug resistance protein 1 (MRP1, clone QCRL-1; 1:100; Millipore), in 40% PBSG at 4° C. overnight. Cells were washed three times with PBS and incubated with secondary antibodies (goat anti-rabbit Texas Red and goat anti-mouse Alexa Fluor 488; 1:500; Invitrogen) for 1 h at 20° C. Cell nuclei were counterstained with 300 nM 4',6-Diamidino-2-pheny-lindoldihydrochloride (DAPI) for 10 min. Cells were then washed three times in PBS and visualized with an Olympus epifluorescence microscope. Images were taken using a Diagnostic Instruments camera run by MetaVue software. For quantitative analysis of BMEC integrity, the percentage of cells expressing frayed tight junctions was counted using BMECs immunolabeled for occludin. Cells were defined as having frayed tight junctions if any cell-cell contact point appeared discontinuous or fuzzy. A minimum of four separate frames and 1000 total cells were counted to obtain a percentage of frayed tight junctions.

Quantitative PCR (qPCR)

Cells were washed once with PBS and dissociated with ACCUTASE (Invitrogen). Total RNA was extracted using an RNEASY Mini Kit (Qiagen) according to the manufacturer's instructions and quantified using a NanoDrop® ND-1000. cDNA was generated from 1 µg of total RNA using Omniscript reverse transcriptase (Qiagen) and an oligo-dT primer (Invitrogen). qPCR was conducted using 1 µL of cDNA and iQ SYBR Green Mastermix (Bio-Rad) on an iCycler (Bio-Rad). Relative expression was quantified between samples using the comparative cycle threshold ($C_t$) method with glyceraldehyde-3-phosphate dehydrogenase (GAPDH) as the housekeeping gene. Triplicate qPCR reactions were used to calculate mean and standard deviation and two independent differentiation experiments were used to confirm biological reproducibility. Primer sequences were as previously reported.

Flow Cytometry

Cells were washed once with PBS and dissociated with ACCUTASE for 5 min, then spun down and fixed in 2% paraformaldehyde for 15 min or 100% methanol for 10 min at 20° C. Cells were blocked and permeabilized in 40% PBSG containing 0.1% TX-100 for 20 min at 20° C. (no TX-100 was included if a surface epitope was being probed or if cells were fixed in methanol) and then incubated with primary antibody diluted in 40% PBSG for 1 h at 20° C. or overnight at 4° C. Antibodies against PECAM-1 (Thermo Fisher), GLUT-1 (Thermo Fisher), VE-cadherin, occludin, claudin-5, p-glycoprotein, BCRP, and MRP1 were used at 1:50 dilution and mouse or rabbit IgG isotype controls were employed at matching concentration. After being washed twice with PBS containing 5% FBS, cells were incubated with goat anti-mouse Alexa Fluor 647 (1:200 dilution) for 30 min at 20° C. After another two washes with PBS containing 5% FBS, cells were analyzed on a FACSCALIBER flow cytometer and the IgG control was used to quantify positive labeling. Elevated GLUT-1 expression was quantified using a GLUT-1/forward scatter plot referenced to baseline GLUT-1 expression measured at day 4 of UM culture.

Western Blots

Cells were washed once with PBS and lysed with RIPA buffer (Pierce, Rockford, Ill., USA). Protein concentration was quantified via BCA assay (Pierce) and proteins were then resolved by SDS-PAGE on 4-20% Tris-Glycine gradient gels (Invitrogen). After transfer to nitrocellulose membranes, blocking was conducted for 1 h in Tris-buffered saline (10 mM Tris-HCl, 100 mM NaCl, pH 7.5) containing 0.1% Tween-20 (TBST) and 5% milk. Samples were probed overnight at 4° C. with anti-VE-cadherin (1:200), anti-claudin-5 (1:250), anti-occludin (1:1000), and anti-beta-actin (Santa Cruz Biotechnology; 1:5000) antibodies diluted in TBST with 5% milk. After being washed five times with TBST, samples were incubated with a peroxidase-conjugated anti-mouse secondary antibody (Invitrogen; 1:2500) for 1 h at 20° C. Protein levels were detected via a SUPERSIGNAL West Pico Chemiluminescent Substrate (Pierce).

Efflux Transporter Substrate Accumulation hiPSC-derived BMECs differentiated in the presence or absence of RA were subcultured onto 12-well plates in EC medium with 10 μM RA or equivalent DMSO depending on the differentiation condition. After 48-72 h, cells were incubated with 10 μM rhodamine 123 (p-glycoprotein substrate; Sigma), 0.4 μCi tritiated colchicine (PerkinElmer), 10 μM 2'-7'-dicholorofluorescein diacetate (DCFDA; Sigma), or 0.25 μCi [$^{14}$C]-doxorubicin in EC medium for 1 h at 37° C. on a rotating platform. Cells were washed three times with phosphate-buffered saline (PBS) and then lysed with PBS containing 5% Triton X-100 (TX-100; Fisher). Fluorescence (485 nm excitation and 530 nm emission) was measured using a plate reader and radioactivity was measured on a scintillation counter. Fluorescence/radioactivity was normalized on a per cell basis by counting trypsin-dissociated cells on a hemacytometer. Duplicate or triplicate wells were used for each condition to calculate mean and standard deviation. Each experiment was conducted twice to ensure biological reproducibility.

Permeability Studies

Permeability experiments were conducted after 24 h in the co-culture phase when maximum TEER was typically observed. To determine $P_e$ values for radiolabeled compounds, each compound was diluted to 0.4 μCi in transport buffer (distilled water with 0.12 M NaCl, 25 mM NaHCO$_3$, 3 mM KCl, 2 mM MgSO$_4$, 2 mM CaCl$_2$, 0.4 mM K$_2$HPO$_4$, 1 mM HEPES, and 0.1% bovine serum albumin [BSA; Sigma]). 200 μL aliquots were extracted from the basolateral chamber every 15 min and replaced by fresh transport buffer. The rate of accumulation of radioactive ligand in the basolateral chamber over the course of 1 h was used to calculate $P_e$ values for [$^{14}$C]-sucrose, [$^3$H]-colchicine, [$^3$H]-diazepam, [$^3$H]-prazosin, and [$^3$H]-vincristine. [$^3$H]-vincristine was purchased from American Radiolabeled Chemicals (St. Louis, Mo., USA), while all other radiolabeled compounds were acquired from PerkinElmer (Waltham, Mass., USA). All compound incubations were conducted at 37° C. and carried out on a rotator. Triplicate filters were used for all permeability studies.

Figure 6:
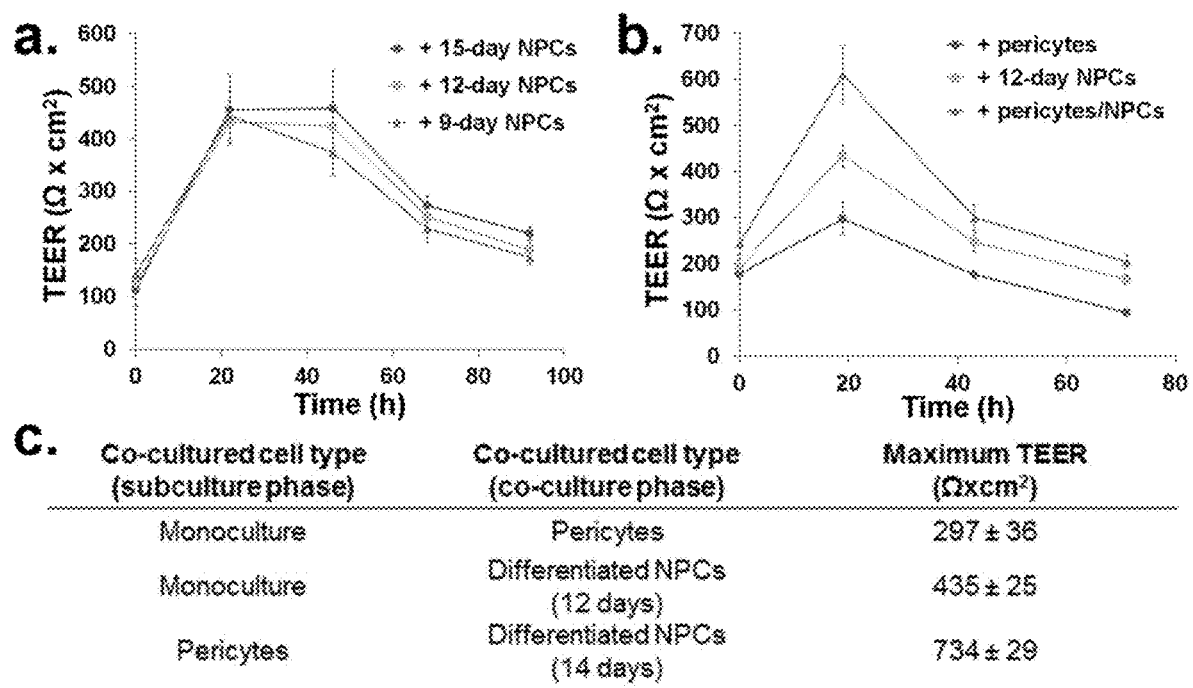
FIG. 6 is a set of diagrams showing effects of hNPC differentiation time and pericyte co-culture on TEER induction in IMR90-4-derived BMECs. a) hNPCs were differentiated for 9, 12, or 15 days and then co-cultured with IMR90-4-derived BMECs in medium containing 10% FBS. b) IMR90-4-derived BMECs were purified and grown to confluence in monoculture or in the presence of pericytes (subculture phase according to FIG. 5). After 24 h, mono-cultured BMECs were co-cultured with pericytes or 12-day differentiated hNPCs, and BMECs that had been co-cultured with pericytes were moved into co-culture with 12-day differentiated hNPCs. Statistical significance was calculated using the student's unpaired t-test. c) Summary of TEER achieved during co-culture experiments. Maximum pericyte/hNPC co-culture TEER is the highest TEER achieved between three biological replicates.
Figure 7:
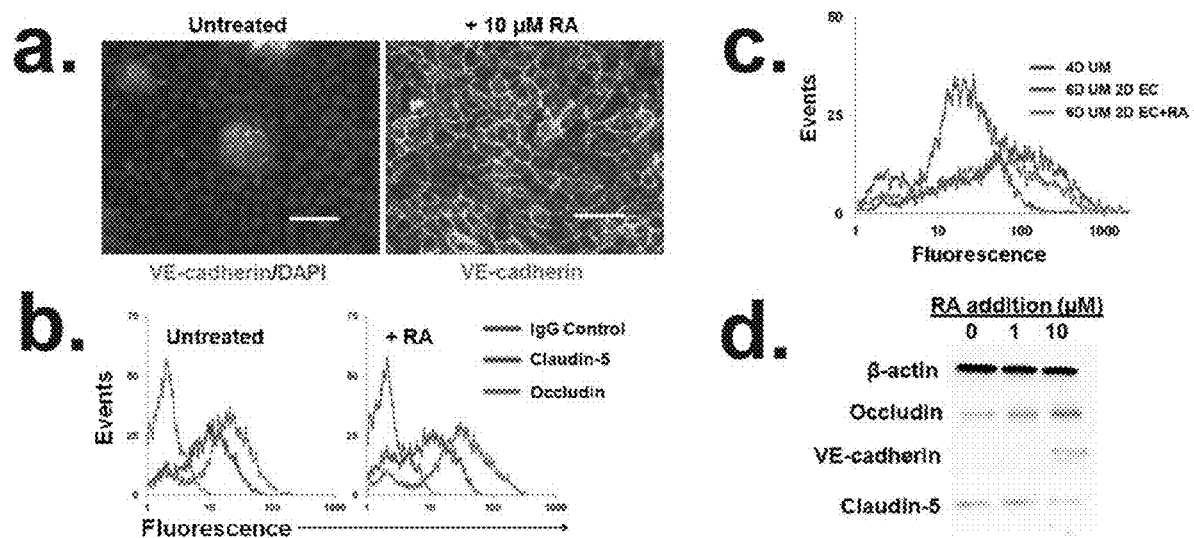
FIG. 7 is a set of diagrams showing the experimental observations after RA treatment where RA treatment modulates protein expression in differentiating IMR90-4 hiPSCs. a) VE-cadherin expression after 48 h of EC medium treatment with or without RA. Scale bars indicate 50 μm. b) Flow cytometry demonstrates increased occludin and decreased claudin-5 expression after 48 h of EC medium treatment with or without RA. Results are representative of three biological replicates. c) The number of GLUT-1$^+$ BMECs is unchanged by RA treatment. Results are representative of two biological replicates. d) Western blots demonstrate increased occludin and VE-cadherin expression due to RA treatment.
Figure 8:
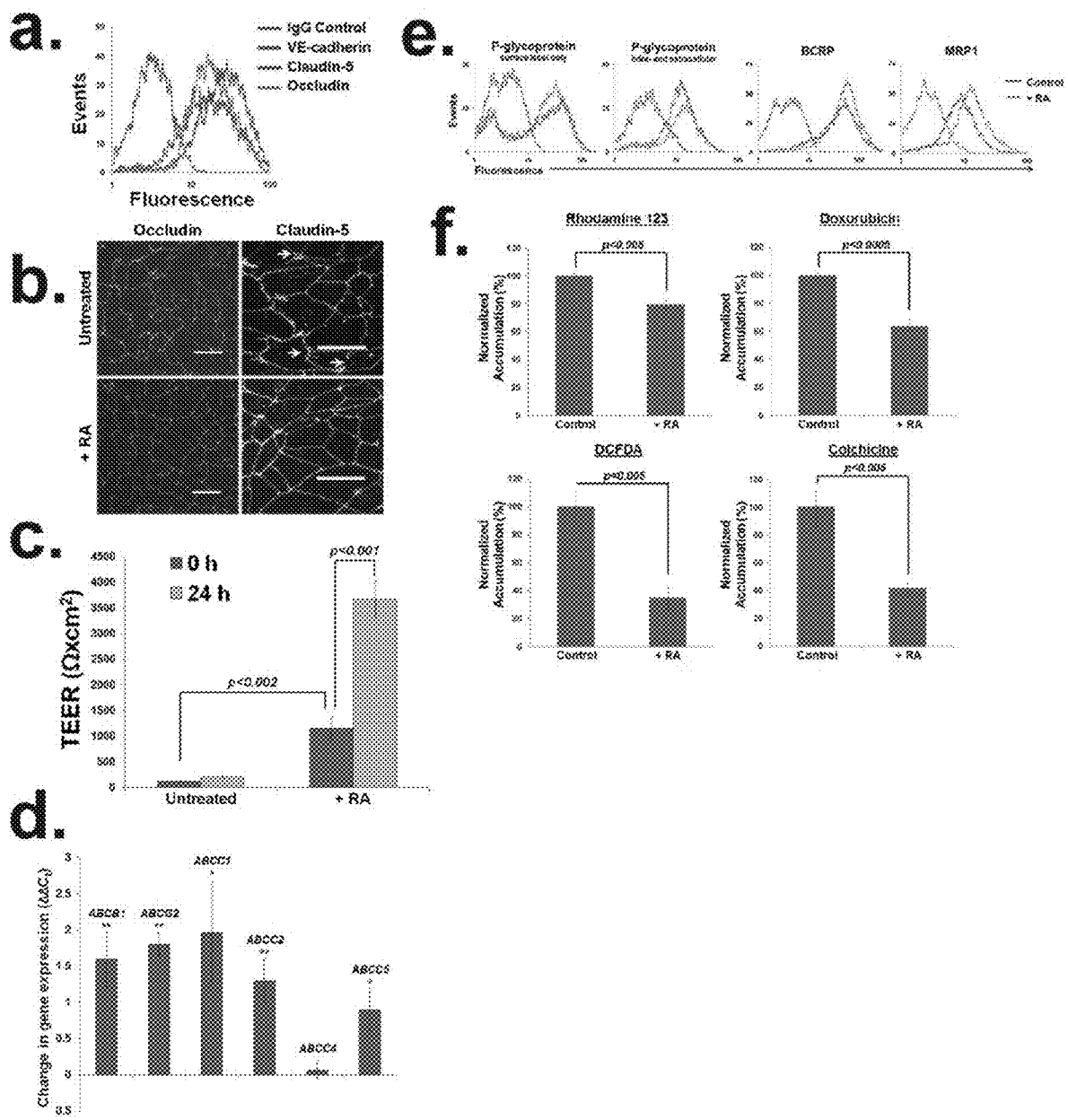
FIG. 8 is a set of diagrams showing passive and active barrier properties in purified RA-treated IMR90-4-derived BMECs. a) Flow cytometry demonstrates purity for VE-cadherin, claudin-5, and occludin. b) Untreated cells possess a large number of frayed tight junction strands (highlighted by arrows) while RA-treated cells possess mostly smooth and continuous tight junctions (quantified in the Results section). Scale bars indicate 50 μm. c) RA-treated BMECs have significantly higher baseline (t=0 h) and maximum TEER (t=24 h) compared to untreated BMECs. Statistical significance was calculated using the student's unpaired t-test. Table 1 summarizes the biological replicates. d) Change in efflux transporter gene expression was examined by qPCR. ABCB1, ABCG2, ABCC1, ABCC2, ABCC5, and STRA6 were upregulated due to RA treatment (positive change in $\Delta\Delta C_t$). ABCC4 and SLC2A1 were unaffected by RA. Results are representative of two biological replicates. Statistical significance was calculated using the student's unpaired t-test (*, p<0.01; **, p<0.005). e) Flow cytometry demonstrates upregulation of p-glycoprotein, BCRP, and MRP1 due to RA treatment compared to a DMSO control. P-glycoprotein shows increased expression only when both the intracellular and extracellular compartments were probed. Results are representative of two biological replicates. f) RA-treated BMECs exhibit decreased accumulation of rhodamine 123, colchicine, doxorubicin, and DCFDA compared to DMSO-treated controls. Results are representative of two biological replicates. Statistical significance was calculated using the student's unpaired t-test.
Figure 9:
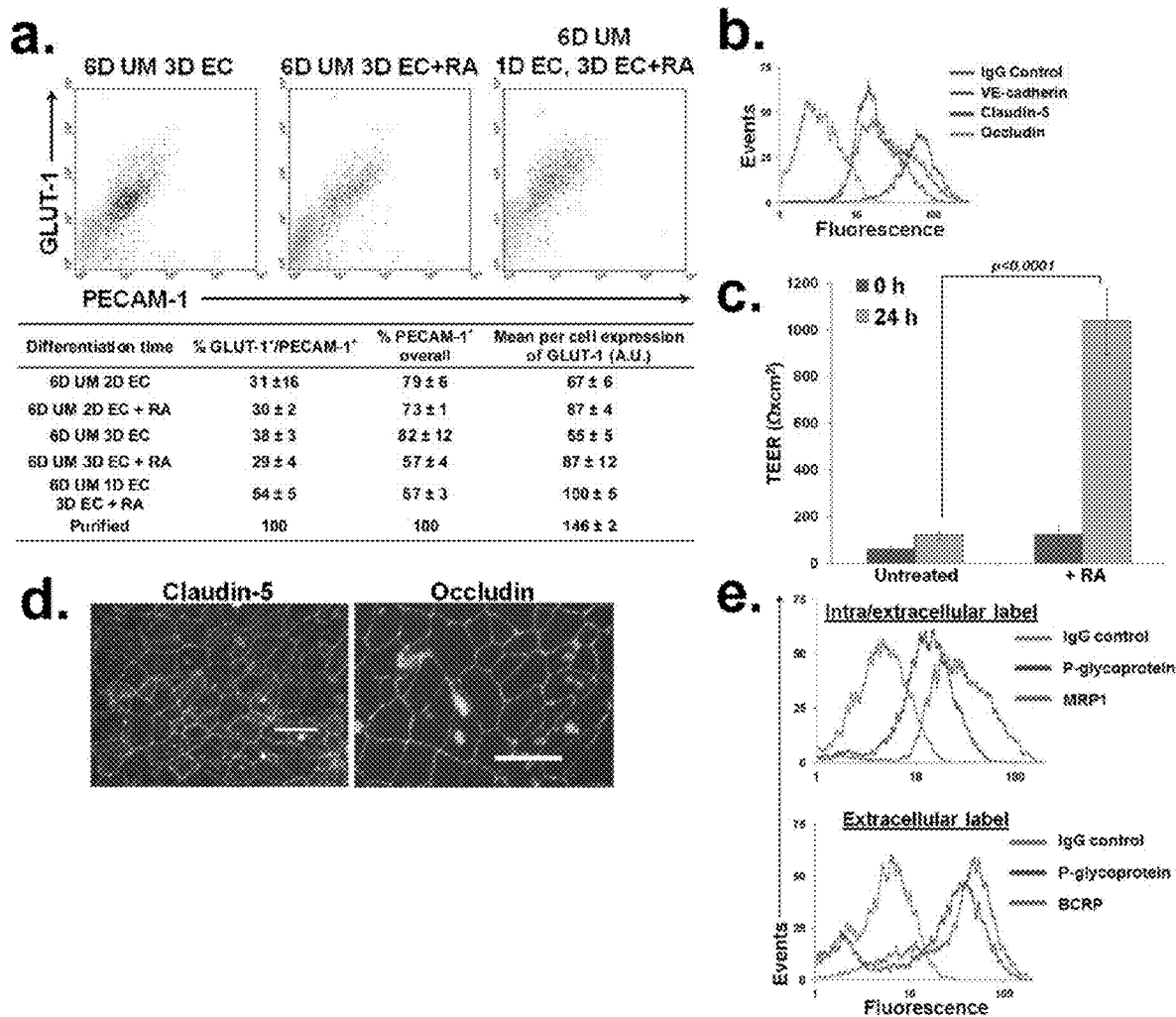
FIG. 9 is a set of diagrams showing that RA can tune BBB properties in H9-derived BMECs. a) Flow cytometry was used to assess BMEC differentiation by monitoring PECAM-1 and GLUT-1 expression. Red dots represent PECAM-1$^+$/GLUT-1$^+$ cells, blue dots represent PECAM-1$^+$/GLUT-1$^-$ cells, and green dots represent PECAM-1$^-$/GLUT-1$^-$ cells. The two color dot plots are indicative of the observed results, which are quantified and summarized in the table. Mean±S.D. was calculated across two biological replicates for each condition. b) After subculture, flow cytometry demonstrates purity of VE-cadherin, claudin-5, and occludin. c) RA-treated BMECs possess significantly elevated TEER. Statistical significance was calculated using the student's unpaired t-test. TEER summary is located in Table 1. d) Immunocytochemical analysis of claudin-5 and occludin demonstrates smooth and continuous tight junctions in purified RA-treated BMECs. e) RA-treated BMECs express MRP1, p-glycoprotein, and BCRP. The number of BMECs expressing these efflux transporters is decreased compared to IMR90-4-derived BMECs. Results are representative of two biological replicates.

Results hiPSC-Derived BMECs Respond to Inductive Cues from hNPC-Derived Astrocytes and Neurons Our previous work demonstrated that hNPCs differentiated for 12 days could induce a BBB response in cultured rat BMECs (Lippmann, et al., 2011). To probe similar conditions with BMECs derived from IMR90-4 hiPSCs, we differentiated hNPCs for 9-15 days and initiated co-culture with IMR90-4-derived BMECs in medium containing 10% FBS. While all co-cultures produced elevated TEER (>400 Ω×cm$^2$), no significant difference was observed with respect to hNPC differentiation time (FIG. 6a). We also compared co-culture with human pericytes (FIG. 5, Scheme A) to 12-day differentiated hNPCs (FIG. 5, Scheme B) and observed that differentiated hNPCs could induce higher TEER than pericytes (FIG. 6b; 435±25 Ω×cm$^2$ vs. 297±36 Ω×cm$^2$; p<0.01). We also tested if pericytes could "prime" the hPSC-derived BMECs for hNPC co-culture, whereby hPSC-derived BMECs were co-cultured with pericytes immediately following purification and then transferred to co-culture with differentiated hNPCs after 24 hours (FIG. 5, Scheme D). This sequential co-culture condition yielded the highest TEER compared to either pericyte or 12-day differentiated hNPC co-culture alone (FIG. 6b; 611±63 Ω×cm$^2$; p<0.02). Thus, hNPC differentiation time was not an important variable for TEER induction, but co-culture with both pericytes and differentiated hNPCs could enhance the TEER response. This optimum condition was tested three times and a maximum TEER of 734±29 Ω×cm$^2$ was achieved (Table 1), indicating high-fidelity barrier formation.

RA Enhances BBB Properties in hPSC-Derived BMECs

IMR90-4-derived BMECs exhibit elevated TEER in response to differentiated hNPCs or primary rat astrocytes. However, this TEER value remains below primary bovine and porcine models (reviewed by Deli et al. (Deli, et al., 2005)) and substantially lower than in vivo measurements (Butt, Jones, et al., 1990). In searching for ideas to improve the fidelity of the hPSC-derived BBB model, we identified all-trans RA as a potential candidate to improve BBB characteristics. BMECs have been shown to express retinol-binding protein and its membrane receptor STRA6 (Kawaguchi, 2007), and RA has been shown to upregulate certain BBB properties in immortalized rodent BMEC lines (El Hafny, et al., 1997; Lechardeur, et al., 1995). Further, a recent genomics study indicates that RA signaling may be upregulated at the BBB (Daneman, et al., 2010(b)). Thus, to test the ability of RA to modulate BBB properties during the differentiation phase (prior to purification), IMR90-4 hiPSCs were differentiated for 6 days in standard unconditioned medium (termed UM) to generate a mixed population of neural cells and immature BMECs as previously described (Lippmann, et al., 2012), and RA was added during the 2 days of EC medium treatment (FIG. 5). We first probed the effects of RA by analyzing adherens junction and tight junction protein expression. Immunocytochemistry and western blot analysis were used to demonstrate that addition of 10 μM RA could induce significant VE-cadherin expression whereas 1 μM of RA could not (FIGS. 7a and 7d). The number of cells with elevated GLUT-1 expression as judged by flow cytometry was unchanged by RA treatment (FIG. 7b). However, RA treatment increased the level of occludin expression (1.8 to 2.9-fold across biological replicates) and decreased the level of claudin-5 expression (1.7-fold), and western blot analysis was used to confirm these results (FIG. 7c-d). To more explicitly probe the molecular and phenotypic effects of RA on BMEC properties, control and RA-treated IMR90-4-derived BMECs were purified by matrix adhesion on either polystyrene plates or Transwell filters and grown to confluence. RA-treated BMECs were judged pure by flow cytometry analysis demonstrating 95-98% positive expression for VE-cadherin, claudin-5, and occludin (FIG. 8a). Immunocytochemical analysis also demonstrated claudin-5 and occludin expression localized to cell-cell borders for both untreated control and RA-treated BMECs. Control IMR90-4-derived BMECs possessed a greater percentage of discontinuous tight junction strands with frayed edges (12.7±7.1%), while RA-treated IMR90-4-derived BMECs displayed almost entirely smooth junctions (1.5±0.9%; FIG. 8b). To correlate junction integrity with physical barrier properties, TEER was measured. Control IMR90-4-derived BMECs demonstrated baseline TEER values from 50-180 Ω×cm$^2$, similar to previous observations, while BMECs that received RA treatment had significantly elevated baseline TEER, ranging from 300-1500 Ω×cm$^2$ (t=0 h; FIG. 8c and Table 1). Once the initial TEER of the monolayer was measured, cells were transferred to EC medium without bFGF or RA (termed modified EC medium) and TEER was re-probed after 24 hours. Under these conditions, RA-treated BMECs exhibited TEER above 2000 Ω×cm$^2$ and often exceeding 3000 Ω×cm$^2$, whereas control BMECs rarely exhibited TEER above 300 Ω×cm$^2$ (FIG. 8c). Across 12 independent biological replicates, RA-treated BMECs possessed an average TEER of 2935±802 Ω×cm$^2$ (Table 1).

These data indicate a significant contribution of RA to the passive barrier properties of IMR90-4-derived BMECs.

RA was next examined for its ability to modulate efflux transporter expression and activity. Efflux transporter genes ABCB1 (encoding for p-glycoprotein), ABCG2 (breast cancer resistance protein, BCRP), ABCC1 (multidrug resistance protein 1, MRP1), ABCC2 (MRP2), and ABCC5 (MRP5) were upregulated due to RA treatment ($\Delta\Delta C_t$ values of 1.6±0.4, 1.8±0.15, 1.97±0.71, 1.3±0.31, and 0.9±0.29, respectively, compared to untreated samples) while ABCC4 (MRP4) was not (FIG. 8d). P-glycoprotein, BCRP, and MRP1 were detected by immunocytochemistry and flow cytometry in RA-treated IMR90-4-derived BMECs (FIG. 12 and FIG. 8e). Flow cytometry indicated upregulation of MRP1 due to RA treatment. To assess efflux transporter activity, purified IMR90-4-derived BMECs were incubated with efflux transporter substrates rhodamine 123 (p-glycoprotein substrate), doxorubicin (p-glycoprotein, BCRP, and MRP substrate), carboxy-2',7'-dichlorofluorescein diacetate (DCFDA; MRP substrate), or colchicine (p-glycoprotein and MRP substrate), and cellular uptake was quantified. RA treatment decreased accumulation of each substrate compared to DMSO-treated controls (rhodamine 123, 1.4-fold; doxorubicin, 1.6-fold; DCFDA, 2.9-fold; colchicine, 2.4-fold) (FIG. 8f). These collective results demonstrate p-glycoprotein, BCRP, and the MRP family are active in RA-treated BMECs and MRP activity may be increased due to RA treatment.

Many of the aforementioned effects of RA were confirmed using the DF19-9-11T hiPSC line to demonstrate the effects were not line-specific. Differentiating DF-19-9-11T-derived BMECs expressed VE-cadherin in response to RA treatment (FIG. 13a). RA-treated DF19-9-11T-derived BMECs possessed smooth and continuous tight junctions after purification (FIGS. 13b-c) and could achieve a maximum TEER of 1968±288 $\Omega \times cm^2$ (FIG. 13d). DF19-9-11T-derived BMECs also demonstrated a 1.5-fold reduction in rhodamine 123 accumulation due to RA treatment (FIG. 13e). RA treatment was also tested on ECs derived from H9 hESCs. In our previously published protocol, (Lippmann, et al., 2012). H9 hESCs produced a mixture of BBB and non-BBB endothelium. We therefore wished to determine if RA could shift the ratio of BBB to non-BBB endothelium in favor of BMECs. As such, we initially used flow cytometry to determine if RA treatment could increase GLUT-1 expression in the differentiating H9 hESCs. Addition of RA during 2 days of EC medium treatment was found to elevate the level of GLUT-1 expression within the BMECs but not the total number of PECAM-1$^+$/GLUT-1$^+$ BMECs (FIG. 9a). If RA treatment was extended for an additional day, a similar trend was observed. The overall number of PECAM-1$^+$ cells also decreased with extended RA treatment, which was perhaps unsurprising since RA can cause proliferation of other cell populations. In any case, none of these treatments generated a majority of PECAM-1$^+$/GLUT-1$^+$ cells without undesired PECAM-1$^+$/GLUT-1$^-$ non-BBB endothelium. We thus began to test random combinations of EC medium and RA and discovered that 6 days of UM treatment, followed by 1 day of EC medium then 3 days of EC medium containing RA (6D UM, 1D EC, 3D EC+RA), could yield a population of cells where a larger majority of PECAM-1$^+$ cells were also GLUT-1$^+$ (FIG. 9a). After purification (FIG. 9b), BMECs treated according to the optimized RA schedule possessed significantly elevated TEER (1039±142 $\Omega \times cm^2$) compared to ECs not receiving RA treatment (120±34 $\Omega \times cm^2$; p<0.0001) (FIG. 9c). The RA-treated BMECs possessed smooth tight junctions (FIG. 9d) and the average TEER using this optimized RA treatment schedule was 646±308 $\Omega \times cm^2$ (Table 1). H9-derived BMECs also expressed p-glycoprotein, BCRP, and MRP1 although cells were not uniformly positive (FIG. 9e). Thus, further optimization of RA treatment and additional factors may be necessary for continued improvement of the BBB phenotype in H9-derived BMECs.

Optimization of the RA-Treated BBB Co-Culture Model

We next utilized RA treatment in the human co-culture model described in FIG. 2. Co-culture of RA-treated IMR90-4-derived BMECs with pericytes increased TEER above the monoculture control (FIG. 10a and Table 2; 1603±53 $\Omega \times cm^2$ vs. 1043±107 $\Omega \times cm^2$; p<0.002) while co-culture with differentiated hNPCs increased TEER even more significantly (FIG. 10a; 2367±116 $\Omega \times cm^2$; p<0.001). When pericytes were added to RA-treated BMECs during the subculture phase (FIG. 5, Schemes C and D), baseline TEER at confluence was significantly enhanced compared to monocultured BMECs (FIG. 10b compared to FIG. 10a; 2068±124 $\Omega \times cm^2$ vs. 579±42 $\Omega \times cm^2$; p<0.0001). If these BMECs were then co-cultured with differentiated hNPCs, TEER was enhanced further (FIG. 10b; 3370±152 $\Omega \times cm^2$); if these same BMECs remained in co-culture with pericytes, the TEER increase was not as significant (FIG. 10b; 2701±53 $\Omega \times cm^2$), which further confirmed sequential pericyte/hNPC co-culture was the optimum condition for increasing barrier properties (p<0.002 comparing pericyte/hNPC co-culture to pericyte co-culture alone). Pericyte/hNPC co-culture was then examined across 7 different co-cultures using hNPCs differentiated for a variety of time periods (10-19 days). TEER exceeded 2500 $\Omega \times cm^2$ in each experiment, validating the robustness of the model (FIG. 10c). A direct comparison between hNPC differentiation days (13 days vs. 19 days) showed no difference in TEER induction (data not shown) and it was observed that hNPCs differentiated for 10 and 14 days across different experiments yielded similar maximum TEER (FIG. 10c). Even with the variability in age and differentiation time among the three cell types (IMR90-4 hiPSCs, pericytes, hNPCs), this model proves extremely reproducible (Table 2).

Our use of medium containing 10% FBS for co-culture was based on previous results demonstrating an improved TEER response in 10% FBS compared to medium containing 1% PDS (Lippmann, et al., 2012). However, in the previous experiments, the medium containing 1% PDS also contained exogenous bFGF. Angiogenic growth factors such as VEGF can increase BBB permeability (Argaw, et al., 2009), leading us to speculate the bFGF may have a negative effect on TEER. Indeed, the experiments described earlier with RA alone demonstrated a significant spike in TEER in medium containing 1% PDS after bFGF had been removed (modified EC medium; FIG. 8c).

Therefore, we utilized modified EC medium to re-test the sequential pericyte/hNPC co-culture system. First, pericyte co-culture with IMR90-4-derived BMECs during the subculture phase was conducted in standard EC medium, which resulted in significantly elevated TEER above a monoculture control (FIG. 11a [t=0]; 3573±175 $\Omega \times cm^2$ vs. 1575±163 $\Omega \times cm^2$; p<0.0001). If a non-neural control (human foreskin fibroblasts) was used in place of pericytes, TEER was elevated above monoculture (FIG. 11a [t=0]; 2106±30 $\Omega \times cm^2$; p<0.01) but well below the TEER induced by pericytes.

After switching to modified EC medium, no TEER difference was observed between the monoculture control and fibroblasts after 24 hours (FIG. 11a; 2474±124 $\Omega \times cm^2$ vs. 2405±366 $\Omega \times cm^2$; p>0.05). In contrast, pericyte co-culture further increased TEER to 4454±174 Ω×cm² and sequential pericyte/hNPC co-culture yielded even higher TEER at the 24 hour time point (FIG. 11a; 5160±318 Ω×cm²; p<0.05). TEER under these optimal conditions (pericytes/hNPCs in modified EC medium) was >5000 Ω×cm² for five out of six separate co-culture experiments with a maximum value of 5352±252 Ω×cm² (FIG. 11b and Table 2). This extremely high TEER correlated with high fidelity tight junctions (FIG. 11c; 1.4±0.6% frayed junctions), although tight junction fidelity was not significantly different from a direct comparison to BMECs only treated with RA (1.5±0.9%).

Also consistent with the aforementioned results (e.g. FIGS. 6a and 10c), the number of days of hNPC differentiation (9-24 days) did not affect the magnitude of TEER. DF19-9-11T-derived BMECs could reach a TEER of 4738±303 Ω×cm² and H9-derived BMECs could reach a TEER of 1675±95 Ω×cm² under these same co-culture conditions, indicating this scheme is generalizable across different hPSC lines (Table 2). Permeability to efflux transporter substrates vincristine, colchicine, and prazosin and passive tracer molecules sucrose and diazepam was measured in the IMR90-4-derived BMECs under optimized co-culture conditions and compared to RA-treated cells without co-culture. Sucrose ($3.2\pm1\times10^{-5}$ cm/min vs. $3.4\pm0.7\times10^{-5}$ cm/min) and diazepam ($1.02\pm0.3\times10^{-3}$ cm/min vs. $1.02\pm0.5\times10^{-3}$ cm/min) were essentially indistinguishable between these conditions. Prazosin ($1.1\pm0.06\times10^{-4}$ cm/min vs. $2\pm0.5\times10^{-4}$ cm/min), vincristine ($2.6\pm0.9\times10^{-5}$ cm/min vs. $3.5\pm0.9\times10^{-5}$ cm/min), and colchicine ($1.5\pm0.7\times10^{-5}$ cm/min vs. $2.3\pm1\times10^{-5}$ cm/min) permeability were all consistently decreased due to pericyte/hNPC co-culture although the decreases were not statistically significant. Overall, the optimized co-culture conditions resulted in extremely high TEER and low permeability to efflux transporter substrates.

TABLE 3

Summary of permeability experiments in IMR90-4-derived BMECs.

| Compound | Average $P_e$ ($10^{-3}$ cm/min) |
|---|---|
| RA treatment only | |
| Sucrose | 0.034 ± 0.007 |
| Diazepam | 1.02 ± 0.51 |
| Prazosin | 0.2 ± 0.05 |
| Vincristine | 0.035 ± 0.009 |
| Colchicine | 0.023 ± 0.0096 |
| RA treatment and optimized neural cell co-culture | |
| Sucrose | 0.032 ± 0.01 |
| Diazepam | 1.02 ± 0.29 |
| Prazosin | 0.11 ± 0.006 |
| Vincristine | 0.026 ± 0.009 |
| Colchicine | 0.015 ± 0.007 |

Mean and standard deviation are calculated from biological replicates. Each compound was tested at least twice. Within each individual experiment, triplicate filters were used to ensure technical reproducibility.

Discussion

The purpose of this work was to construct a renewable, high-fidelity human BBB co-culture model using hPSCs and hNPCs. In the process, we identified RA as a significant modulator of BMEC properties during hPSC differentiation. Some prior studies have shown RA can regulate general vascular growth in vivo (Lai, et al., 2003) and in vitro (Saito, et al., 2007). Early BBB studies with RA demonstrated its ability to upregulate γ-glutamyl transpeptidase and p-glycoprotein in immortalized rat brain endothelial cell lines (El Hafny, et al., 1997; Lechardeur, et al., 1995), and more recently, a genomics study that profiled mouse brain endothelium compared to liver and lung endothelium suggested RA-mediated signaling was enriched at the BBB (Daneman, et al., 2010(b)). RA was added only during the EC medium treatment phase after initial neuroectoderm/BBB specification because early RA addition to hPSCs can direct differentiation away from a neuroectoderm fate (Metallo, et al., 2008).

RA treatment was initially observed to increase occludin and VE-cadherin expression. Occludin gene expression has been shown to be more highly expressed at the BBB compared to peripheral endothelia (Daneman, et al., 2010 (b)) and therefore may be correlated to improved passive barrier properties. RA treatment also increased expression of p-glycoprotein, BCRP, and MRP1, and increased efflux activity was confirmed for p-glycoprotein and the MRP family. Other nuclear receptor ligands such as pregnenolone-16alpha-carbonitrile and dexamethasone have been shown to regulate p-glycoprotein and MRP2 (Ott, Fricker, et al., 2009; Bauer, et al., 2004; Bauer, et al., 2008), possibly indicating redundant mechanisms of efflux transporter regulation between nuclear receptor families. Efflux transporter activity can also be regulated by endogenous small molecules such as the sex hormone 17-β-estradiol (Hartz, et al., 2010), and similar mechanisms could be responsible for modulating transporter activity independent of transcription and translation in the in vitro system. We also noted that RA addition influences the ratio of BBB to non-BBB endothelium in the differentiating H9 hESC cultures. Because RA has been shown to increase EC proliferation in vitro, it is possible that RA induces proliferation in BMECs but not non-BBB ECs, allowing the BMECs to "outcompete" the non-BBB ECs before and after subculture. It is also possible that RA, along with other known soluble factors (Daneman, et al., 2009; Kuhnert, et al., 2010; Anderson, et al., 2011; Stenman, et al., 2008; Cullen, et al., 2011), contributes to the initial induction of BBB properties, but in vivo work would be needed to confirm this hypothesis.

While RA improved the passive and active barrier properties in hPSC-derived BMECs, co-culture with differentiated hNPCs further improved passive barrier function. In constructing an all-human model composed of hPSCs and hNPCs, we sought to simplify the timing of differentiation for each cell type. Fortunately, hNPCs could be differentiated for 9-24 days with no outstanding difference in TEER induction, which greatly simplifies the alignment of hPSC and hNPC differentiation and co-culture. We have also demonstrated in this study that co-culture with pericytes prior to co-culture with differentiated hNPCs can more effectively enhance TEER than either cell type alone, which agrees with results in various rodent systems using primary isolations of pericytes, astrocytes, and BMECs (Nakagawa, et al., 2009; Nakagawa, et al., 2007).

Overall, this hPSC-derived BMEC/pericyte/differentiated hNPC system represents the first BBB model constructed from renewable sources. Pericytes, which share the basement membrane with endothelial cells in capillaries and play important roles in endothelial maturation and survival, as well as specific roles in BBB development (reviewed extensively in (Winkler, Bell, et al., 2011)), have previously been cultured for twenty weeks with over forty population doublings (Crisan, et al., 2008). Those results indicate pericytes can potentially be derived from a small primary source and expanded significantly. The fetal brain pericytes used in our study were purchased commercially and one vial was expanded in large enough quantities to conduct all experiments. hNPCs, which are derived from primary fetal tissue and have long been recognized for their extensive self-renewal capabilities (Wright, et al., 2003), can be expanded as an unlimited supply of neural cells. Furthermore, the rapidly-expanding field of hPSC technology is likely to eventually make these primary sources unnecessary. Recent progress has been made in the generation of human astroglial progenitors and immature astrocytes from hPSCs that can associate with brain vessels after transplantation into mice (Krencik, et al., 2011). Progress has also been made towards differentiating cells with pericyte characteristics from hPSCs (Dar, et al., 2012; Lian, et al., 2010). Based on these collective reports, it is highly plausible that a human BBB model could be created entirely from hPSC sources.

Perhaps the most striking result from this model is the absolute level of TEER achieved. The combination of RA treatment with pericyte and differentiated NPC co-culture resulted in hPSC-derived BMECs possessing a maximum TEER in excess of 5000 $\Omega \times cm^2$, which is several fold higher than the closest animal model and more than 10-fold higher than any published human model (Deli, et al., 2005). Classic experiments performed by Crone and Olesen measured an average TEER of 1870 $\Omega \times cm^2$ in the frog BBB, while experiments on the brains of maturing rats (above 21 days of gestation) by Butt and co-workers measured an average TEER of 1490±170 $\Omega \times cm^2$ in brain arterial vessels and 918±127 $\Omega \times cm^2$ in venous vessels (Butt, Jones, et al., 1990; Crone, Olesen, 1982)—therefore, the average TEER measured in these experiments fall well below the level of TEER achieved in the hPSC-derived BMECs.

However, Crone and Olesen measured a maximum TEER value of 2976 $\Omega \times cm^2$ in the frog BBB and speculate that based on their theoretically calculated value of conductance, one might expect a maximum TEER of 4000 $\Omega \times cm^2$. Similarly, Butt and co-workers measured a maximum value of 5900 $\Omega \times cm^2$ in the rat brain and stated in their report that "any potential deterioration of the preparation would tend to lower the measured values, so it is conceivable that the higher figures reflect the true resistance of the blood-brain barrier" (Butt, Jones, et al., 1990). Further, a separate study by Smith and Rapoport estimated an in vivo TEER of 8000 $\Omega \times cm^2$ at the rat BBB based on measured permeability coefficients of radioisotopic ions (Smith, et al., 1986). Thus, the TEER achieved by our BBB model is not outside the measured or predicted range of in vivo TEER and in fact is as close to an in vivo barrier as have ever been measured in an in vitro model. Permeability to small molecules was also altered by RA treatment and pericyte/hNPC co-culture.

RA-treated IMR90-4-derived BMECs in monoculture demonstrated decreased permeability to efflux transporter substrates colchicine and vincristine compared to IMR90-4-derived BMECs co-cultured with rat astrocytes. Co-culture of pericytes and differentiated hNPCs with RA-treated IMR90-4-derived BMECs also resulted in a slight reduction in permeability to efflux transporter substrates. Astrocytes have been shown to upregulate p-glycoprotein expression and function in primary bovine BMECs, while we and others have shown mild increases in p-glycoprotein gene expression due to astrocyte co-culture in primary rat BMECs but another study demonstrated downregulation under similar conditions in mouse BMECs. Intriguingly, the all-human model does not possess permeability coefficients that agree with in vivo uptake data measured in rodents. IMR90-4-derived BMECs co-cultured with rat astrocytes previously showed excellent correlation between measured in vitro permeabilities of small molecule drugs and in vivo uptake coefficients ($R^2$=0.98; diazepam>prazosin>colchicine>vincristine>sucrose). The all-human model exhibits reduced vincristine and colchicine permeability, whereby these compounds become less permeable than sucrose, which is dissimilar from rodent in vivo and in vitro data (Perriere, et al., 2007). However, the hCMEC/D3 immortalized human BMEC line shows a similar trend, where sucrose permeability ($1.65 \times 10^{-3}$ cm/min) is similar to colchicine permeability (approximately $1.6 \times 10^{-3}$ cm/min, estimated from graphical data) and above vincristine permeability (approximately $0.75 \times 10^{-3}$ cm/min, estimated from graphical data) (Weksler, et al., 2005). Many variations in efflux transporter gene expression are observed between different species (Warren, et al, 2009) and the hPSC-derived BMECs derived in this study, when pushed towards a more in vivo-like phenotype by RA and pericyte/hNPC co-culture, may reflect such species differences.

In conclusion, we provide evidence that RA can modulate BBB properties in hPSC-derived BMECs. Co-culture of these RA-treated BMECs with human pericytes and human astrocyte/neuron mixtures derived from hNPCs yields a fully human BBB model with substantial passive barrier properties and improved efflux transporter activity. Based on TEER and small molecule permeability data, and the ability to generate unlimited quantities of hPSCs and hNPCs, we propose this all-human model has utility for screening large compound libraries for potential human brain uptake. Furthermore, the three tested hPSC lines, which are derived from different sources and via different reprogramming methods, could all generate BMECs with substantially elevated TEER, indicating these results could be reproduced in other laboratories using hESCs or hiPSCs derived under various conditions.

REFERENCES

1. Zlokovic, B. V., *The blood-brain barrier in health and chronic neurodegenerative disorders*. Neuron, 2008. 57(2): p. 178-201.
2. Pardridge, W. M., *The blood-brain barrier: bottleneck in brain drug development*. NeuroRx, 2005. 2(1): p. 3-14.
3. Deli, M. A., et al., *Permeability studies on in vitro blood-brain barrier models: physiology, pathology, and pharmacology*. Cell Mol Neurobiol, 2005. 25(1): p. 59-127.
4. Nakagawa, S., et al., *A new blood-brain barrier model using primary rat brain endothelial cells, pericytes and astrocytes*. Neurochem Int, 2009. 54(3-4): p. 253-63.
5. Nakagawa, S., et al., *Pericytes from brain microvessels strengthen the barrier integrity in primary cultures of rat brain endothelial cells*. Cell Mol Neurobiol, 2007. 27(6): p. 687-94.
6. Weidenfeller, C., C. N. Svendsen, and E. V. Shusta, *Differentiating embryonic neural progenitor cells induce blood-brain barrier properties*. J Neurochem, 2007. 101 (2): p. 555-65.
7. Lippmann, E. S., et al., *Blood-brain barrier modeling with co-cultured neural progenitor cell-derived astrocytes and neurons*. J Neurochem, 2011. 119(3): p. 507-520.
8. Daneman, R., et al., *Wnt/beta-catenin signaling is required for CNS, but not non-CNS, angiogenesis*. Proc Natl Acad Sci USA, 2009. 106(2): p. 641-6.
9. Daneman, R., et al., *Pericytes are required for blood-brain barrier integrity during embryogenesis*. Nature, 2010(a). 468(7323): p. 562-6.
10. Kuhnert, F., et al., *Essential regulation of CNS angiogenesis by the orphan G protein-coupled receptor GPR124*. Science, 2010. 330(6006): p. 985-9.

11. Lee, S. W., et al., *SSeCKS regulates angiogenesis and tight junction formation in blood-brain barrier*. Nat Med, 2003. 9(7): p. 900-6.
12. Wosik, K., et al., *Angiotensin II controls occludin function and is required for blood brain barrier maintenance: relevance to multiple sclerosis*. J Neurosci, 2007. 27(34): p. 9032-42.
13. Cecchelli, R., et al., *Modelling of the blood-brain barrier in drug discovery and development*. Nat Rev Drug Discov, 2007. 6(8): p. 650-61.
14. Bernas, M. J., et al., *Establishment of primary cultures of human brain microvascular endothelial cells to provide an in vitro cellular model of the blood-brain barrier*. Nat. Protoc., 2010. 5(7): p. 1265-72.
15. Rubin, L. L., et al., *A cell culture model of the blood-brain barrier*. J Cell Biol, 1991. 115(6): p. 1725-35.
16. Weksler, B. B., et al., *Blood-brain barrier-specific properties of a human adult brain endothelial cell line*. Faseb J, 2005. 19(13): p. 1872-4.
17. Lippmann, E. S., et al., *Derivation of blood-brain barrier endothelial cells from human pluripotent stem cells*. Nat Biotechnol, 2012. 30(8): p. 783-91.
18. Butt, A. M., H. C. Jones, and N. J. Abbott, *Electrical resistance across the blood-brain barrier in anaesthetized rats: a developmental study*. J Physiol, 1990. 429: p. 47-62.
19. Crone, C. and S. P. Olesen, *Electrical resistance of brain microvascular endothelium*. Brain Res, 1982. 241(1): p. 49-55.
20. Kawaguchi, R., et al., *A membrane receptor for retinol binding protein mediates cellular uptake of vitamin A*. Science, 2007. 315(5813): p. 820-5.
21. El Hafny, B., et al., *Modulation of P-glycoprotein activity by glial factors and retinoic acid in an immortalized rat brain microvessel endothelial cell line*. Neurosci Lett, 1997. 236(2): p. 107-11.
22. Lechardeur, D., et al., *Induction of blood-brain barrier differentiation in a rat brain-derived endothelial cell line*. Exp Cell Res, 1995. 220(1): p. 161-70.
23. Daneman, R., et al., *The mouse blood-brain barrier transcriptome: a new resource for understanding the development and function of brain endothelial cells*. PLoS One, 2010(b). 5(10): p. e13741.
24. Argaw, A. T., et al., *VEGF-mediated disruption of endothelial CLN-5 promotes blood-brain barrier breakdown*. Proc Natl Acad Sci USA, 2009. 106(6): p. 1977-82.
25. Lai, L., et al., *Retinoic acid regulates endothelial cell proliferation during vasculogenesis*. Development, 2003. 130(26): p. 6465-74.
26. Saito, A., et al., *All-trans retinoic acid induces in vitro angiogenesis via retinoic acid receptor: possible involvement of paracrine effects of endogenous vascular endothelial growth factor signaling*. Endocrinology, 2007. 148(3): p. 1412-23.
27. Metallo, C. M., et al., *Retinoic acid and bone morphogenetic protein signaling synergize to efficiently direct epithelial differentiation of human embryonic stem cells*. Stem Cells, 2008. 26(2): p. 372-80.
28. Ott, M., G. Fricker, and B. Bauer, *Pregnane X receptor (PXR) regulates P-glycoprotein at the blood-brain barrier: functional similarities between pig and human PXR*. J Pharmacol Exp Ther, 2009. 329(1): p. 141-9.
29. Bauer, B., et al., *Pregnane X receptor up-regulation of P-glycoprotein expression and transport function at the blood-brain barrier*. Mol Pharmacol, 2004. 66(3): p. 413-9.
30. Bauer, B., et al., *Coordinated nuclear receptor regulation of the efflux transporter, Mrp2, and the phase-II metabolizing enzyme, GSTpi, at the blood-brain barrier*. J Cereb Blood Flow Metab, 2008. 28(6): p. 1222-34.
31. Hartz, A. M., et al., *17-beta-Estradiol: a powerful modulator of blood-brain barrier BCRP activity*. J Cereb Blood Flow Metab, 2010. 30(10): p. 1742-55.
32. Anderson, K. D., et al., *Angiogenic sprouting into neural tissue requires Gpr124, an orphan G protein-coupled receptor*. Proc Natl Acad Sci USA, 2011. 108(7): p. 2807-12.
33. Stenman, J. M., et al., *Canonical Wnt signaling regulates organ-specific assembly and differentiation of CNS vasculature*. Science, 2008. 322(5905): p. 1247-50.
34. Cullen, M., et al., *GPR124, an orphan G protein-coupled receptor, is required for CNS-specific vascularization and establishment of the blood-brain barrier*. Proc Natl Acad Sci USA, 2011. 108(14): p. 5759-64.
35. Winkler, E. A., R. D. Bell, and B. V. Zlokovic, *Central nervous system pericytes in health and disease*. Nat. Neurosci., 2011. 14(11): p. 1398-405.
36. Crisan, M., et al., *A perivascular origin for mesenchymal stem cells in multiple human organs*. Cell Stem Cell, 2008. 3(3): p. 301-13.
37. Wright, L. S., et al., *Gene expression in human neural stem cells: effects of leukemia inhibitory factor*. J Neurochem, 2003. 86(1): p. 179-95.
38. Krencik, R., et al., *Specification of transplantable astroglial subtypes from human pluripotent stem cells*. Nat Biotechnol, 2011. 29(6): p. 528-34.
39. Dar, A., et al., *Multipotent Vasculogenic Pericytes from Human Pluripotent Stem Cells Promote Recovery of Murine Ischemic Limb*. Circulation, 2012. 125: p. 87-99.
40. Lian, Q., et al., *Functional mesenchymal stem cells derived from human induced pluripotent stem cells attenuate limb ischemia in mice*. Circulation. 121(9): p. 1113-23.
41. Smith, Q. R. and S. I. Rapoport, *Cerebrovascular permeability coefficients to sodium, potassium, and chloride*. J Neurochem, 1986. 46(6): p. 1732-42.
42. Perriere, N., et al., *A functional in vitro model of rat blood-brain barrier for molecular analysis of efflux transporters*. Brain Res, 2007. 1150: p. 1-13.
43. Warren, M. S., et al., *Comparative gene expression profiles of ABC transporters in brain microvessel endothelial cells and brain in five species including human*. Pharmacol Res, 2009. 59(6): p. 404-13.

We claim:

1. A method of creating a retinoic acid (RA)-enhanced fully-human blood-brain barrier (BBB), wherein the transendothelial electrical resistance (TEER) of the BBB formed is greater than 4000 Ohm×cm$^2$ in an optimized endothelial cell medium (OECM) wherein the OECM does not contain basic fibroblast growth factor (bFGF), the method comprising the steps of:
   (a) culturing a mixture of neural cells and PCAM-1$^+$ GLUT-1$^+$ brain microvascular endothelial cells (BMECs) in the presence of about 10 μM-20 μM RA, wherein the mixture of neural cells and BMECs was produced from the differentiation of human pluripotent stem cells (hPSCs);
   (b) purifying the PCAM-1$^+$ GLUT-1$^+$ BMECs from the mixture of neural cells and PCAM-1GLUT-1BMECs in the presence of about 10 μM-20 μM RA;
   (c) culturing the purified PCAM-1$^+$ GLUT-1 BMECs on a permeable insert in liquid communication with human pericytes in OECM for at least 24 hours, wherein the pericytes are not attached to the permeable insert; and (d) co-culturing the confluent monolayer of PCAM-1$^+$ GLUT-1$^+$ BMECs of (c) on a permeable membrane with a human cell type selected from the group consisting of human pericytes and day 9-24 differentiated human neural progenitor cells (NPCs) in OECM for at least 24 hours, wherein the human cells are not attached to the permeable insert and are in liquid communication with the BMECs, thereby creating fully-human BBB with a TEER of greater than 4000 Ohm×cm$^2$.

2. The method of claim 1, wherein the human cell type in step (d) is human pericytes.

3. The method of claim 1, wherein step (c) comprises human pericytes co-cultured with BMECs within 30 minutes after the purification of BMECs.

4. The method of claim 1, wherein the human cell type in step (d) is day 9-24 differentiated hNPCs, wherein the fully-human BBB is created with TEER of greater than 5000 Ohm×cm$^2$.

5. A retinoic acid (RA)-enhanced human blood-brain barrier (BBB) in optimized endothelial cell medium (OECM) having a TEER greater than 4000 Ohm×cm$^2$, wherein the OECM does not contain basic fibroblast growth factor (bFGF), the BBB comprising:

a) purified RA-treated human PCAM-1$^+$ GLUT-1$^+$ BMECs which form a confluent monolayer on a permeable insert, wherein the RA-treated human PCAM-1$^+$ GLUT-1$^+$ BMECs have been purified from a mixture of human neural cells and human BMECs cultured in medium comprising 10 µM-20 µM RA for at least 24 hours, wherein the mixture of neural cells and BMECs was produced from the differentiation of human pluripotent stem cells (hPSCs) in the presence of 10 µM-20 µM RA; and b) human pericytes, wherein the pericytes are not attached to the permeable insert and are in liquid communication with the BMECs, wherein the pericytes were co-cultured with the purified RA-treated BMECs within 30 minutes of purification in OECM for at least 24 hours such that the purified BMECs form a monolayer on the permeable insert, and wherein the purified RA-treated BMECs are confluent, and wherein said RA-enhanced BBB with TEER of greater than 4000 Ohm×cm$^2$ is produced by the method of claim 2.

6. A retinoic acid (RA)-enhanced human blood brain barrier (BBB) in optimized endothelial cell medium (OECM) having a TEER greater than 5000 Ohm×cm$^2$, wherein the OECM does not contain basic fibroblast growth factor (bFGF), comprising:

a) purified RA-treated human PCAM-1$^+$ GLUT-1$^+$ BMECs that form a monolayer on a permeable insert, wherein the RA-treated human BMECs have been purified from a mixture of human neural cells and human BMECs cultured in medium comprising 10 µM-20 µM RA for at least 24 hours, wherein the mixture of human neural cells and BMECs was produced from the differentiation of human pluripotent stem cells (hPSCs) in the presence of 10 µM-20 µM RA and the purified RA treated BMECs were subsequently co-cultured within 30 minutes of purification with pericytes in OECM for at least 24 hours; and b) days 9-24 differentiated hNPCs in liquid communication with RA-treated human BMECs and not attached to the permeable insert, wherein the hNPCs have been co-cultured with the RA-purified BMECs in OECM for at least 24 hours, wherein said RA-enhanced BBB with TEER of greater than 5000 Ohm×cm$^2$ is produced by the method of claim 4.

\* \* \* \* \*